US012565475B2

(12) United States Patent
Choi et al.

(10) Patent No.: US 12,565,475 B2
(45) Date of Patent: Mar. 3, 2026

(54) SMALL MOLECULE COMPOUND INHIBITING SIGNAL TRANSMISSION PATH OF TLR7 AND TLR9 AND USE THEREOF

(71) Applicant: AJOU UNIVERSITY INDUSTRY-ACADEMIC COOPERATION FOUNDATION, Suwon-si (KR)

(72) Inventors: Sangdun Choi, Suwon-si (KR); Haseeb Muhammad, Suwon-si (KR); Mahesh Patra, Suwon-si (KR); Yang-Seon Choi, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 1035 days.

(21) Appl. No.: 17/630,043

(22) PCT Filed: Jul. 23, 2020

(86) PCT No.: PCT/KR2020/009732

§ 371 (c)(1),
(2) Date: Jan. 25, 2022

(87) PCT Pub. No.: WO2021/020807

PCT Pub. Date: Feb. 4, 2021

(65) Prior Publication Data

US 2022/0259155 A1 Aug. 18, 2022

(30) Foreign Application Priority Data

Jul. 26, 2019 (KR) ........................ 10-2019-0090580

(51) Int. Cl.
*C07D 233/88* (2006.01)
*C07D 405/04* (2006.01)

(52) U.S. Cl.
CPC ......... *C07D 233/88* (2013.01); *C07D 405/04* (2013.01)

(58) Field of Classification Search
CPC ............................ C07D 233/88; C07D 405/04
USPC .......................................................... 514/398
See application file for complete search history.

(56) References Cited

U.S. PATENT DOCUMENTS

| | | | |
|---|---|---|---|
| 7,410,975 | B2 | 8/2008 | Lipford et al. |
| 2007/0032531 | A1 | 2/2007 | Smith et al. |
| 2013/0143927 | A1 | 6/2013 | Whitten et al. |
| 2013/0317032 | A1 | 11/2013 | Vo et al. |

FOREIGN PATENT DOCUMENTS

| | | | |
|---|---|---|---|
| EP | 2 399 578 A1 | 12/2011 | |
| WO | 02/088113 A1 | 11/2002 | |
| WO | 2007/058990 A2 | 5/2007 | |
| WO | 2019/035971 A1 | 2/2019 | |
| WO | 2019/136147 A1 | 7/2019 | |
| WO | 2019/241631 A1 | 12/2019 | |
| WO | 2019/241641 A2 | 12/2019 | |

OTHER PUBLICATIONS

Cancer [online], [retrieved on Jul. 6, 2007] Retrieved from the Internet, URL: http://www.nim.nih.gov/medlineplus/cancer.html (Year: 2007).*

Lala et al., Role of nitric oxide in tumor progression: Lessons from experimental tumors, Cancer and Metastasis Reviews (1998), 17 91-106 (Year: 1998).*

Golub et al., Molecular Classification of Cancer: Class Discovery and Class Prediction by Gene Expression Monitoring, Science (1999), vol. 286, 531-537 (Year: 1999).*

Fardokht A. Abulwerdi et al., Selective Small-Molecule Targeting of a Triple Helix Encoded by the Long noncoding RNA, *MALAT1*, ACS chemical biology, 2019, DOI: 10.1021/acschembio.8b00807, vol. 14 pp. 223-235 (13 pages).

CAS Registry No. 827326-84-1, Entered STN: Feb. 8, 2005, STN Files: Chemcats, (1 page total).

CAS Registry No. 939893-73-4, Entered STN: Jun. 28, 2007, STN Files: CA, Caplus, Chemcats, Toxcenter, Uspatfull, (3 pages total).

Korean Office Action dated Jun. 6, 2024 in Application No. 10-2019-0090580.

Communication issued Nov. 13, 2024 in Korean Application No. 10-2019-0090580.

(Continued)

*Primary Examiner* — Kristin A Vajda
(74) *Attorney, Agent, or Firm* — Sughrue Mion, PLLC

(57) ABSTRACT

A compound of Chemical Formula 1 or a pharmaceutically acceptable salt thereof is disclosed. The compound inhibits a toll-like receptor (TLR) signaling pathway. A composition containing the compound and uses thereof are disclosed. The novel compound blocks the TNF-α secretion by inhibiting the expression and activation of NF-κB- and MAPK-related proinflammatory genes, and thus can be utilized as a therapeutic agent for many autoimmune diseases, such as systemic lupus erythematosus, psoriasis and psoriatic arthritis, associated with a hyperactivity of a nucleic acid:

[Chemical Formula 1]

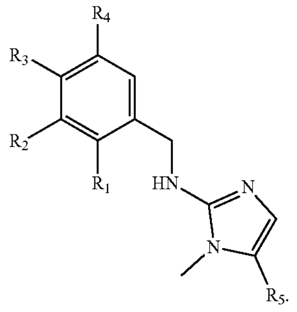

20 Claims, 26 Drawing Sheets

(56) References Cited

OTHER PUBLICATIONS

International Search Report for PCT/KR2020/009732 dated Oct. 26, 2020.
Written Opinion for PCT/KR2020/009732 dated Oct. 26, 2020.
Extended European Search Report dated May 25, 2023 in Application No. 20847286.0.
Roman Barbalat et al., "Nucleic Acid Recognition by the Innate Immune System", Annual Review of Immunology, 2011, vol. 29, pp. 185-214 (32 pages total).
Sandra N. Lester et al., "Toll-Like Receptors in Antiviral Innate Immunity", Journal of Molecular Biology, 2014, vol. 426, pp. 1246-1264 (20 pages total).
Gregory M. Barton et al., "Intracellular localization of Toll-like receptor 9 prevents recognition of self DNA but facilitates access to viral DNA", Nature Immunology, Jan. 2006, vol. 7, No. 1, pp. 49-56 (8 pages total).
Franck J. Barrat et al., "Nucleic acids of mammalian origin can act as endogenous ligands for Toll-like receptors and may promote systemic lupus erythematosus", The Journal of Experimental Medicine, Oct. 17, 2005, vol. 202, No. 8, pp. 1131-1139 (9 pages total).
Christina M. Lau et al., "RNA-associated autoantigens activate B cells by combined B cell antigen receptor/Toll-like receptor 7 engagement", The Journal of Experimental Medicine, Nov. 7, 2005, vol. 202, No. 9, pp. 1171-1177 (7 pages total).
Arthur M. Krieg et al., "Toll-like receptors 7, 8, and 9: linking innate immunity to autoimmunity", Immunological Reviews, 2007, vol. 220, pp. 251-269 (19 pages total).
Claudia Calcaterra et al., "Critical Role of TLR9 in Acute Graft-versus-Host Disease", The Journal of Immunology, 2008, vol. 181, No. 9, pp. 6132-6139 (8 pages total).
Deepak M.W. Balak et al., "IMO-8400, a toll-like receptor 7, 8, and 9 antagonist, demonstrates clinical activity in a phase 2a, randomized, placebo-controlled trial in patients with moderate-to-severe plaque psoriasis", Clinical Immunology, 2017, vol. 174, pp. 63-72 (36 pages total).
Nobutaka Hanagata, "Structure-dependent immunostimulatory effect of CpG oligodeoxynucleotides and their delivery system", International Journal of Nanomedicine, 2012, vol. 7, 2181-2195 (15 pages total).
Takumi Kawasaki et al., "Toll-like receptor signaling pathways", Frontiers in Immunology, Sep. 25, 2014, vol. 5, Article 461, pp. 1-8 (9 pages total).
Marion Jurk et al., "Human TLR7 or TLR8 independently confer responsiveness to the antiviral compound R-848", Nature Immunology, Jun. 2022, vol. 3, No. 6, p. 499 (1 pages total).
Gregory Sliwoski et al., "Computational Methods in Drug Discovery", Pharmacological Reviews, Jan. 2014, vol. 66, vol. 1, pp. 334-395 (62 pages total).
Umeharu Ohto et al., "Toll-like Receptor 9 Contains Two DNA Binding Sites that Function Cooperatively to Promote Receptor Dimerization and Activation", Immunity, 2018, vol. 48, No. 4, pp. 1-10 (15 pages total).
Deepak B. Salunke et al., "Structure—Activity Relationships in Human Toll-like Receptor 8-Active 2,3-Diamino-furo[2,3-c]pyridines", Journal of Medicinal Chemistry, 2012, vol. 55, No. 18, pp. 8137-8151 (15 pages total).
Alenka Kuznik et al., "Mechanism of Endosomal TLR Inhibition by Antimalarial Drugs and Imidazoquinolines", The Journal of Immunology, 2011, vol. 186, No. 8, pp. 4794-4804 (12 pages total).
John J. Irwin et al., "Zinc: A Free Tool to Discover Chemistry for Biology", Journal of Chemical Information and Modeling, 2012, vol. 52, No. 7, 1757-1768 (12 pages total).
Manabu Watanabe et al., "Dihydropyrrolo[2,3-d]pyrimidines: Selective Toll-like Receptor 9 Antagonists from Scaffold Morphing Efforts", ACS Medicinal Chemistry Letters, Oct. 2, 2014, vol. 5, No. 11, pp. 1-6 (7 pages total).
Maria Zatsepin et al., "Computational Discovery and Experimental Confirmation of TLR9 Receptor Antagonist Leads", Journal of Chemical Information and Modeling, Aug. 18, 2016, vol. 56, No. 9, pp. 1835-1846 (33 pages total).
Andrew Waterhouse et al., "Swiss-Model: homology modelling of protein structures and complexes", Nucleic Acids Research, 2018, vol. 46, No. 1, pp. W296-W303 (8 pages total).
Zhikuan Zhang et al., "Structural Analysis Reveals that Toll-like Receptor 7 Is a Dual Receptor for Guanosine and Single-Stranded RNA" Immunity, Oct. 18, 2016, vol. 45, No. 4, pp. 1-12 (13 pages total).
Umeharu Ohto et al., "Structural basis of CpG and inhibitory DNA recognition by Toll-like receptor 9". Nature, Apr. 30, 2015,, vol. 520, No. 7549, pp. 702-705 (17 pages total).
Euna Yoo et al., "Structure—Activity Relationships in Toll-like Receptor 7 Agonistic 1H-Imidazo [4,5-c]pyridines", Organic & Biomolecular Chemistry, vol. 11, No. 38, pp. 6526-6545 (20 pages total) 2013.

* cited by examiner

TIC10

TLR9 $IC_{50}$ = 14.36 μM

TLR7 $IC_{50}$ = 15.84 μM

TIC10-7

TLR9 $IC_{50}$ = 6.71 µM

TLR7 $IC_{50}$ = 6.79 µM

TIC10

TIC10-3

TIC10-7

TIC10-8

TIC10-10

TIC10-11

FIG. 5B

| Name | SMILES | IUPAC Name | MW (g/mol) |
|---|---|---|---|
| TIC10 | COc1ccc(cc1)-c1cnc(NCc2cccc(OC)c2O)n1C | 2-methoxy-6-({[5-(4-methoxyphenyl)-1-methyl-1H-imidazol-2-yl]amino}methyl)phenol | 339.395 |
| TIC10-3 | CCOc1ccc(cc1)-c1cnc(NCc2ccc(OC)c(OC)c2OC)n1C | 5-(4-ethoxyphenyl)-1-methyl-N-[(2,3,4-trimethoxyphenyl)methyl]-1H-imidazol-2-amine | 397.475 |
| TIC10-7 | COc1ccc(CNc2ncc(-c3ccc4OCOc4c3)n2C)c(OC)c1 | 5-(2H-1,3-benzodioxol-5-yl)-N-[(2,4-dimethoxyphenyl)methyl]-1-methyl-1H-imidazol-2-amine | 367.405 |
| TIC10-8 | CCOc1ccc(cc1)-c1cnc(NCc2cccc(OC)c2OC)n1C | N-[(2,3-dimethoxyphenyl)methyl]-5-(4-ethoxyphenyl)-1-methyl-1H-imidazol-2-amine | 367.449 |
| TIC10-10 | CCOc1ccc(CNc2ncc(-c3ccc(OC)cc3)n2C)cc1OC | N-[(4-ethoxy-3-methoxyphenyl)methyl]-5-(4-methoxyphenyl)-1-methyl-1H-imidazol-2-amine | 367.449 |
| TIC10-11 | COc1cc(CNc2ncc(-c3ccc(Cl)cc3)n2C)cc(OC)c1OC | 5-(4-chlorophenyl)-1-methyl-N-[(3,4,5-trimethoxyphenyl)methyl]-1H-imidazol-2-amine | 387.86 |

SMALL MOLECULE COMPOUND INHIBITING SIGNAL TRANSMISSION PATH OF TLR7 AND TLR9 AND USE THEREOF

CROSS REFERENCE TO RELATED APPLICATIONS

This application is a National Stage of International Application No. PCT/KR2020/009732 filed Jul. 23, 2020, claiming priority based on Korean Patent Application No. 10-2019-0090580 filed Jul. 26, 2019.

TECHNICAL FIELD

The present invention relates to a small-molecule compound that inhibits a toll-like receptor (TLR) signaling pathway, and more particularly to a compound represented by a specific chemical formula, a composition for inhibiting TLR comprising the same, and a composition for preventing or treating an autoimmune disease or inflammatory disease comprising the composition for inhibiting TLR.

BACKGROUND ART

Toll-like receptor 7 (TLR7) and TLR9 are activated forms of essential innate immune receptors located in the endosomal compartments of cells. These receptors recognize nucleic acid fragments of viral/bacterial origin and mediate inflammation through a MyD88 (myeloid differentiation primary response 88)-dependent signaling cascade (Barbalat R. et al. (2011) *Annu. Rev. Immunol.* 29:185-214). Stimulation of TLR7 by viral single-stranded RNA (ssRNA) or stimulation of TLR9 by single-stranded CpG motif-containing DNA (CpG-DNA) activates various types of cells, particularly dendritic cells, natural killer cells, macrophages, B cells, and T cells. The activated cell population immediately secretes several proinflammatory cytokines such as tumor necrosis factor-α (TNF-α) and interleukin-6 (IL-6), and antiviral cytokines such as type I interferons (IFNs; IFN-α/β) and IFN-γ (Lester S. N. & Li K. (2014) *J. Mol. Biol.* 426(6):1246-1264).

Endosomal TLRs are evolutionarily programmed for intracellular localization and evade spontaneous recognition of circulating or endogenous nucleic acids (Barton G. M., Kagan J. C., & Medzhitov R. (2006) *Nat. Immunol.* 7(1): 49-56). Nevertheless, these receptors are activated by host nucleic acids under certain pathogenic or genetic conditions to thus form autoantibodies that induce the onset of diseases such as systemic lupus erythematosus. Unmethylated CpG DNA rarely occurs in mammalian genomes. However, TLR9 is involved in several mammalian DNA-induced inflammatory diseases (Barrat F. J. et al. (2005) *J. Exp. Med.* 202(8): 1131-1139). This situation triggers an immune response against the host molecule that induces the expression of autoantibodies, resulting in tissue damage. The sera in SLE patients contain nucleic acids bound to antibodies that protect nucleic acids from enzymes and facilitate entry into cells, high mobility group box 1 proteins, ribonuclear proteins, etc. A cell-surface receptor called immunoglobulin γ Fc region receptor IIa is known to mediate antibody-bound self-DNA/RNA uptake (Lau C. M. et al. (2005) *J. Exp. Med.* 202(9):1171-1177). Nucleic acids of the autoimmune complex ultimately activate endosomal TLRs and thus upregulate the production of type I IFNs (Krieg A. M. & Vollmer J. (2007) *Immunol. Rev.* 220:251-269).

The nucleic acid cargo of the endolysosomal compartment is able to stimulate TLR and prepares the immune system for autoimmune antibody production. Increased production of self-reactive antibodies and increased formation of immune complexes are hallmarks of the pathogenesis of SLE, Sjogren's syndrome, and a variety of other diseases. In addition, TLR7- and TLR9-mediated hyperimmune responses may contribute to liver damage, lung infection, and graft rejection in the host (Calcaterra C. et al. (2008) *J. Immunol.* 181(9):6132-6139). Of reported endosomal TLR antagonists, an oligonucleotide-based molecule and a single low-molecular-weight compound CPG52364 developed by Pfizer (NCT00547014) have entered clinical trials (Balak D. M. et al. (2017) *Clin. Immunol.* 174:63-72). However, synthetic oligonucleotides have several problems, such as administration via injection, high synthesis costs, and uncertain immunogenicity (Hanagata N. (2012) *Int. J Nanomedicine* 7:2181-2195).

Accordingly, the present inventors have made great efforts to develop a low-molecular-weight TLR7/TLR9 dual inhibitor for oral administration as a future drug candidate for anti-inflammatory drugs, identified a primary lead that inhibits TLR7/TLR9, called TLR inhibitory compound 10 (TIC10; 2-methoxy-6-({[5-(4-methoxyphenyl)-1-methyl-1H-imidazol-2-yl]amino}methyl)phenol), and ascertained that a derivative thereof, namely TIC10-7 (5-(2H-1,3-benzodioxol-5-yl)-N-[(2,4-dimethoxyphenyl)methyl]-1-methyl-1H-imidazol-2-amine), inhibits both TLR9 and TLR7, and exhibits an equivalent effect upon cell-based bioassay. Particularly, the compound TIC10-7 inhibits TLR7- and TLR9-mediated TNF-α secretion and has greater efficacy than the primary lead TIC10, and moreover, ligand inhibition occurs through suppression of NF-κB- and MAPK-related proinflammatory gene expression, thus culminating in the present invention.

The information described in the Background Art is only for improving understanding of the background of the present invention, and it is not to be construed as including information forming the related art already known to those of ordinary skill in the art to which the present invention belongs.

SUMMARY OF THE INVENTION

It is an object of the present invention to provide a small-molecule compound having TLR inhibitory activity and a composition for inhibiting TLR (toll-like receptor) comprising the same.

It is another object of the present invention to provide a composition for preventing or treating an autoimmune disease comprising the small-molecule compound or the composition for inhibiting TLR.

It is still another object of the present invention to provide a composition for preventing or treating an inflammatory disease comprising the small-molecule compound or the composition for inhibiting TLR.

It is yet another object of the present invention to provide a method of preventing or treating an autoimmune disease or inflammatory disease comprising administering the small-molecule compound or the composition for inhibiting TLR.

It is a further object of the present invention to provide the use of the small-molecule compound or the composition for inhibiting TLR for the prevention or treatment of an autoimmune disease or inflammatory disease.

It is still a further object of the present invention to provide the use of the small-molecule compound or the composition for inhibiting TLR for the manufacture of a medicament for the prevention or treatment of an autoimmune disease or inflammatory disease.

In order to accomplish the above objects, the present invention provides a compound represented by Chemical Formula 1 below or a pharmaceutically acceptable salt thereof.

[Chemical Formula 1]

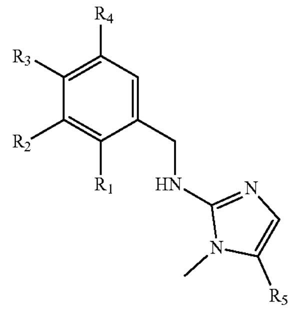

In Chemical Formula 1

$R_1$ to $R_5$ are each independently a hydrogen atom, straight or branched alkyl, amino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, in which the alkyl or alkoxy is $C_{1-30}$, the cycloalkyl is $C_{3-30}$, the allyl is $C_{2-30}$, the aryl is $C_{6-30}$, and the heteroaryl and heterocycloalkyl comprise a heteroatom selected from among fluorine (F), oxygen (O), sulfur (S), and nitrogen (N).

In addition, the present invention provides a composition for inhibiting TLR (toll-like receptor) comprising the compound or the pharmaceutically acceptable salt thereof.

In addition, the present invention provides a composition for preventing or treating an autoimmune disease comprising the compound or the composition for inhibiting TLR.

In addition, the present invention provides a composition for preventing or treating an inflammatory disease comprising the compound or the composition for inhibiting TLR.

In addition, the present invention provides a method of preventing or treating an autoimmune disease or inflammatory disease comprising administering the compound or the composition for inhibiting TLR.

In addition, the present invention provides the use of the compound or the composition for inhibiting TLR for the prevention or treatment of an autoimmune disease or inflammatory disease.

In addition, the present invention provides the use of the compound or the composition for inhibiting TLR for the manufacture of a medicament for the prevention or treatment of an autoimmune disease or inflammatory disease.

BRIEF DESCRIPTION OF DRAWINGS

FIGS. 2A-2C show ligand-binding sites of TLR9 models considered for molecular docking, in which FIG. 2A shows site I of TLR9 corresponding to the small molecule binding site of TLR7, FIG. 2B shows site Ia recognizing a 5'-xCx DNA motif, and FIG. 2C shows site II of TLR9 to which CpG DNA binds, Chain A being represented in green and Chain B being represented in blue, and the detailed structure of the binding site being enlarged on the right side of each panel.

FIGS. 3A-3D show the initial cell-based screening for the identification of TLR7/TLR9 antagonists, in which FIG. 3A shows results of cytotoxicity assay for 16 high-scoring virtual hits in the murine macrophage cell line RAW 264.7, in which cells were treated with 10 or 50 μM of each ligand for 24 hours and cell viability was monitored by an MTT assay, mean±SEM of the results of three independent experiments being calculated using a two-tailed paired Student's t-test (*$p<0.05$, $p<0.01$, *$p<0.001$), ligands showing significant cytotoxicity being represented in red, FIG. 3B shows test results of the potential agonistic activity of eight selected non-cytotoxic compounds, in which cells were stimulated with the compounds alone for 24 hours or were pretreated for 1 hour followed by stimulation with a TLR9 agonist ODN2395 (0.5 μM) for 4 hours, and the secretion of mouse TNF-α was measured by ELISA, FIG. 3C shows the effect of the ligand on inhibiting TLR9 activation, and FIG. 3D shows the effect of the ligand on inhibiting TLR7 activation, in which cells were pretreated with the ligand for 1 hour and stimulated with a TLR9-specific agonist ODN2395 (0.5 μM) or a TLR7-specific agonist imiquimod (3.61 μM) for 4 hours, and TNF-α secretion was measured by ELISA, mean±SEM of the results of three independent experiments being calculated using a two-tailed paired Student's t-test (*$p<0.05$, $p<0.01$, *$p<0.001$).

FIGS. 4A-4F show the relative inhibitory activities of TIC10 and TIC10-7 against TLR7 and TLR9 activation, in which FIG. 4A shows the effect of the ligand on inhibiting TLR9 activation, FIG. 4B shows the effect of the ligand on inhibiting TLR7 activation, in which RAW 264.7 cells were pretreated with 10 or 50 μM TIC10 or a selected derivative for 1 hour followed by stimulation with a TLR9 agonist ODN2395 or a TLR7 agonist imiquimod for 4 hours, and the secretion level of TNF-α was measured by ELISA, FIG. 4C shows the inhibition % of TLR9-mediated TNF-α secretion by TIC10 and TIC10-7, FIG. 4D shows the inhibition % of TLR7-mediated TNF-α secretion by TIC10 and TIC10-7, in which cytokine secretion values from two independent experiments were averaged and normalized with respect to 0% as a negative control (untreated) and 100% as a positive control (agonist alone), and $IC_{50}$ values were calculated using a four-parametric robust regression method, FIG. 4E shows the 2D chemical structure of the primary lead TIC10, and FIG. 4F shows the 2D chemical structure of the potent TIC-analogue TIC10-7.

FIGS. 5A and 5B show the two-dimensional structures of the active ligands identified from the cell-based assay, in which FIG. 5A shows ligands including TIC10 identified as a preliminary hit having TLR9 inhibitory activity, a derivative TIC10-7 identified as a potent TLR7/TLR9 dual inhibitor, and the like, and FIG. 5B shows SMILES, IUPAC names, and molecular weights of the active ligands (TIC10 and derivatives thereof).

FIGS. 6A-6H show the receptor specificity and signaling pathway inhibitory effect of TIC10-7, in which FIGS. 6A to 6G show the effect of TIC10-7 on inhibiting toll-like receptor (TLR) family members, in which RAW 264.7 cells were pretreated with a control (−), DMSO (0.25%), and TIC10-7 (10 or 20 μM) for 1 hour and then stimulated with agonists selective for TLR1/2 (Pam3CSK), TLR2/6 (FSL-1), TLR4 (LPS), TLR7 (Imiquimod), and TLR9 (ODN2395) for 4 hours, and stimulated with an agonist selective for TLR3 (poly I:C) for 24 hours, the secretion level of TNF-α was measured by ELISA, and only for TLR8, a human monocytic cell line (THP-1) was used, THP-1 cells were differentiated with phorbol 12-myristate 13-acetate (PMA) for 48 hours, treated with TIC10-7 for 1 hour, and then treated with TL8-506 as a TLR8 agonist for 4 hours, human TNF-α secretion being measured by ELISA, and FIG. 6H shows the results of Western blots showing a decrease in phosphorylation of the p65 subunit (p-p65) of NF-κB (nuclear factor k-light-chain-enhancer of activated B cells) and phosphorylation of MAPKs (mitogen-activated protein kinases: extracellular-signal-regulated kinase (p-ERK), p38-MAPK (p-p38), and c-Jun N-terminal kinase (p-JNK)) after treatment with TIC10-7 for 1 hour, in which RAW 264.7 cells were stimulated with ODN2395 as a TLR9 agonist for 15 or 30 minutes in the presence or absence of TIC10-7 (20 μM), and total protein extraction and immunoblotting were performed using primary and secondary antibodies for each protein.

FIGS. 7A and 7B show the interactions of TIC10-7 with the ligand binding cavities of TLR7 and TLR9, in which FIG. 7A shows the binding mode of TIC10-7 in the small molecule binding cavity of the TLR7 extracellular domain, in which the detailed interactions of the ligand with residues around about 5 Å therefrom are shown in the right magnified view, and FIG. 7B shows analogous binding of TIC10-7 to the extracellular domain of TLR9, in which the interactions of the ligand occurring around about 5 Å therefrom are shown in the right zoomed view, Chain A is represented in green and Chain B is represented in blue, and the ligand is modeled as a ball-and-stick, residues of the B chain being labeled with an asterisk (*), hydrogen bonds being shown as dashed line, and numbers representing distances in Å unit.

DETAILED DESCRIPTION AND PREFERRED EMBODIMENTS OF THE INVENTION

Figure 1:
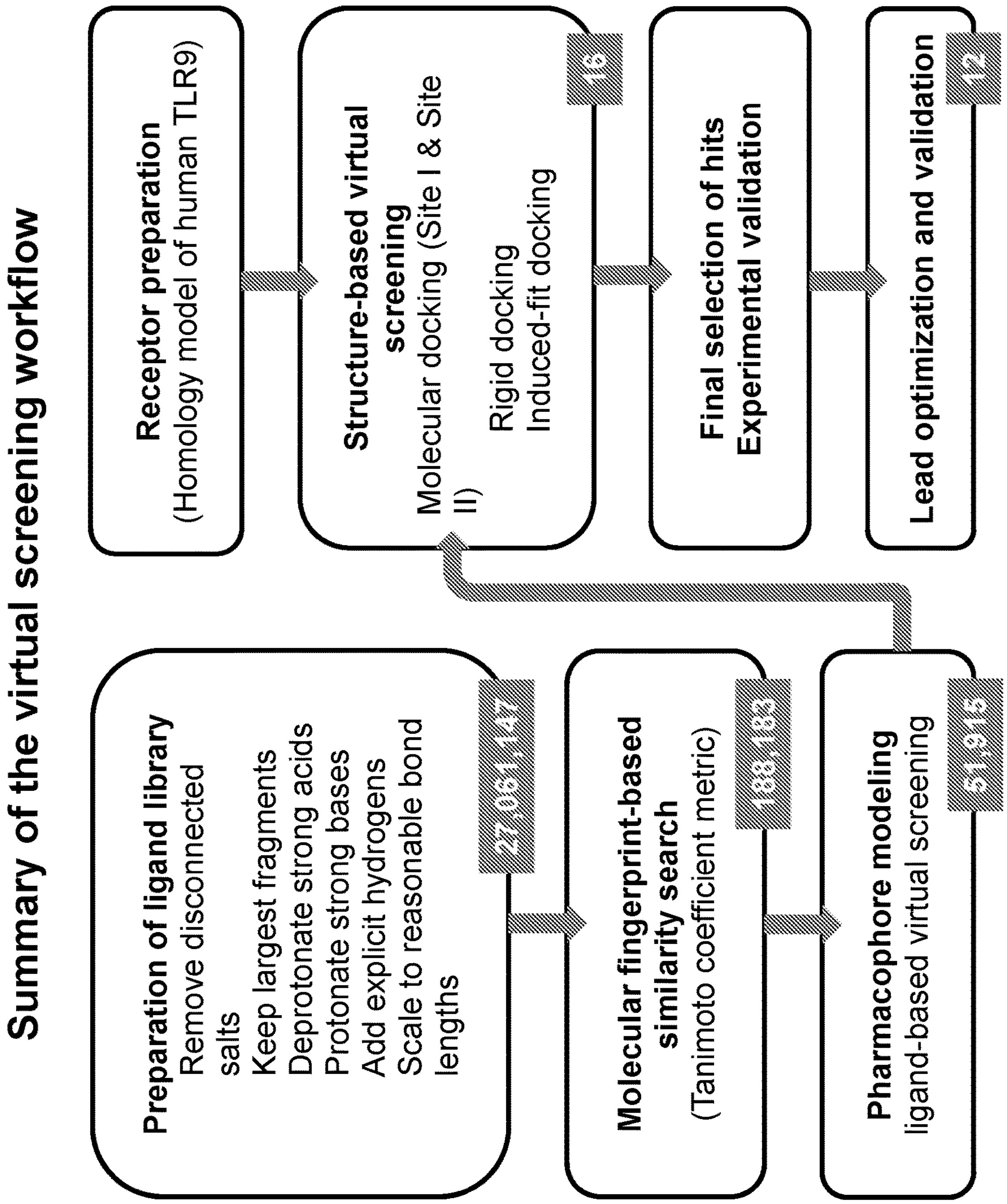
FIG. 1 shows a computational workflow for identifying the primary lead, in which the dark gray box represents the number of ligands that progressed to the subsequent step, and the ligands generated from pharmacophore screening are input for separate rigid and induced-fit dockings.

Unless otherwise defined, all technical and scientific terms used herein have the same meanings as those typically understood by those skilled in the art to which the present invention belongs. In general, the nomenclature used herein is well known in the art and is ordinarily used.

Aberrant secretion of proinflammatory cytokines from immune cells is a major cause of inflammatory diseases such as systemic lupus erythematosus and rheumatoid arthritis. Toll-like receptor 7 (TLR7) and TLR9 sequestered to the endosomal compartments of dendritic cells and macrophages are mainly associated with the pathogenesis and proliferation of these diseases. Therefore, the development of drugs against the dysregulated endosomal TLRs is essential in order to suppress systemic inflammation.

In the present invention, TLR inhibitory compound 10 (TIC10) and a derivative thereof (TIC10-7), which are novel low-molecular-weight compounds showing dual inhibition of TLR7 and TLR9 signaling pathways, were obtained using the principle of computer-aided drug discovery. Specifically, TIC10-7 inhibited TLR7- and TLR9-mediated TNF-α (tumor necrosis factor-α) secretion in a concentration-dependent manner. Although TIC10-7 slightly inhibited the activation of TLR3 or TLR8, it had no effect on cell-surface TLR (TLR1/2, TLR2/6, or TLR4), and exhibited an effect only on TLR7 and TLR9. Based on the results of Western blot assay, TIC10-7 downregulated the phosphorylation of phosphorylation of p65-subunit of NK-κB (nuclear factor κ-light-chain-enhancer) and MAPK (mitogen-activated protein kinases: extracellular-signal-regulated kinase (p-ERK), p38-MAPK (p-p38), and c-Jun N-terminal kinase (p-JNK)) induced by a TLR9 agonist (ODN2395). These results indicate that the novel ligand, TIC10-7, is an endosomal TLR (TLR7 and TLR9)-specific dual inhibitor interfering with the expression of MAPK- and NF-κB-mediated proinflammatory genes.

Accordingly, in one aspect, the present invention is directed to a compound represented by Chemical Formula 1 below or a pharmaceutically acceptable salt thereof.

[Chemical Formula 1]

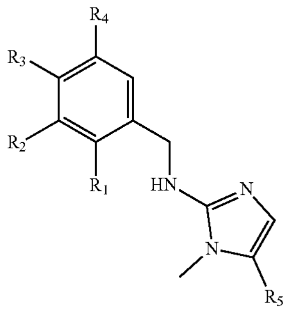

In Chemical Formula 1, $R_1$ to $R_5$ are each independently a hydrogen atom, straight or branched alkyl, amino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, in which the alkyl or alkoxy is $C_{1-30}$, the cycloalkyl is $C_{3-30}$, the allyl is $C_{2-30}$, the aryl is $C_{6-30}$, and the heteroaryl and heterocycloalkyl comprise a heteroatom selected from among fluorine (F), oxygen (O), sulfur (S), and nitrogen (N).

In the present invention, the alkyl or alkoxy is preferably $C_{1-12}$, more preferably $C_{1-6}$, and most preferably $C_{1-4}$.

As used herein, the term "$C_{1-30}$ alkyl" refers to a monovalent linear or branched saturated hydrocarbon moiety having 1 to 30 carbon atoms and consisting only of carbon and hydrogen atoms. Examples of the alkyl group include, but are not limited to, methyl, ethyl, propyl, isopropyl, butyl, isobutyl, sec-butyl, tert-butyl, and the like. Examples of "branched alkyl" include isopropyl, isobutyl, tert-butyl, and the like.

The term "$C_{1-30}$ alkoxy" refers to a chemical formula —O—$C_{1-30}$ alkyl, and includes, for example, methoxy, ethoxy, isopropoxy, tert-butoxy, and the like, but is not limited thereto.

Specific examples of the term "halogen (or halo)" include fluorine (F), chlorine (Cl), bromine (Br), and iodine (I).

The term "$C_{6-30}$ aryl" includes at least one ring having a shared pi electron system, for example a monocyclic or fused-ring polycyclic group (i.e. rings that share adjacent pairs of carbon atoms). Unless otherwise defined herein, the aryl may include phenyl, naphthyl, and biaryl. In an embodiment of the present invention, the aryl is an aromatic ring having 6 to 30 carbon atoms.

The term "$C_{3-30}$ cyclic alkyl" refers to a cyclic saturated hydrocarbon moiety having 5 to 6 carbon atoms and consisting only of carbon and hydrogen atoms. Examples of such a cyclic alkyl group include, but are not limited to, cyclopentyl, cyclohexyl, and the like.

Unless otherwise defined, the term "heteroaryl" refers to a 5- or 6-membered aromatic ring comprising 1 to 4 heteroatoms selected from the group consisting of N, O, and S, or a bicyclic ring in which the heteroaryl ring is fused to a benzene ring or another heteroaryl ring. Examples of monocyclic heteroaryl include thiazolyl, oxazolyl, thiophenyl, furanyl, pyrrolyl, imidazolyl, isoxazolyl, isothiazolyl, pyrazolyl, triazolyl, triazinyl, thiadiazolyl, tetrazolyl, oxadiazolyl, pyridinyl, pyridazinyl, pyrimidinyl, pyrazinyl, and groups similar thereto, but are not limited thereto. Examples of bicyclic heteroaryl include indolyl, azaindolyl, indolinyl, benzothiophenyl, benzofuranyl, benzimidazolyl, benzoxazolyl, benzisoxazolyl, benzothiazolyl, benzothiadiazolyl, benzotriazolyl, quinolinyl, isoquinolinyl, purinyl, furopyridinyl, and groups similar thereto, but are not limited thereto.

The term "heterocycloalkyl" refers to a saturated or partially unsaturated 5- to 9-membered carbocyclic ring comprising 1 to 3 heteroatoms selected from among N, O, and S, in addition to carbon atoms. For example, heterocyclyl is azetidinyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, dihydroindolyl, dihydrofuryl, dihydroimidazolinyl, dihydrooxazolyl, tetrahydropyridinyl, dihydropyranyl, dihydrobenzofuranyl, benzodioxolyl, or benzodioxanyl.

In the present invention, $R_5$ may be represented by the structure of Chemical Formula 2 below.

[Chemical Formula 2]

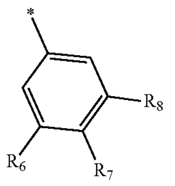

In Chemical Formula 2, $R_6$ or $R_8$ is each independently a hydrogen atom, hydroxy, straight or branched alkyl, cycloalkyl, alkoxy, aryl, or halogen, or at least two of $R_6$ to $R_8$ are linked to each other to form a cycloalkyl or heterocycloalkyl, in which the alkyl or alkoxy is $C_{1-30}$, the cycloalkyl is $C_{3-30}$, the aryl is $C_{6-30}$, and the heterocycloalkyl comprises a heteroatom selected from among fluorine (F), oxygen (O), sulfur (S), and nitrogen (N).

The alkyl or alkoxy is preferably $C_{1-12}$, more preferably $C_{1-6}$, and most preferably $C_{1-4}$.

In the present invention, when any two of $R_6$ to $R_8$ are linked to form a cyclo structure, the remaining one may be a hydrogen atom.

In Chemical Formula 2, * represents a position bound to the backbone imidazole structure.

In the present invention, $R_5$ may be represented by the structure of Chemical Formula 3 below.

[Chemical Formula 3]

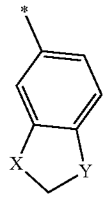

In Chemical Formula 3,

X or Y is each independently oxygen (O), sulfur (S), or nitrogen (N).

In the present invention, $R_1$ is a hydrogen atom, hydroxy, or methoxy, $R_2$ is a hydrogen atom or methoxy, $R_3$ is a hydrogen atom, methoxy, or ethoxy, $R_4$ is a hydrogen atom or methoxy, and $R_5$ is chlorophenyl, methoxyphenyl, ethoxyphenyl, or 1,3-benzodioxolyl, but the present invention is not limited thereto.

In an embodiment of the present invention, $R_5$ may be p-chlorophenyl, p-methoxyphenyl, p-ethoxyphenyl, or 1,3-benzodioxolyl.

In the present invention, the compound described above may be any one compound selected from the group consisting of Chemical Formula 1-1 to Chemical Formula 1-6 below.

[Chemical Formula 1-1]

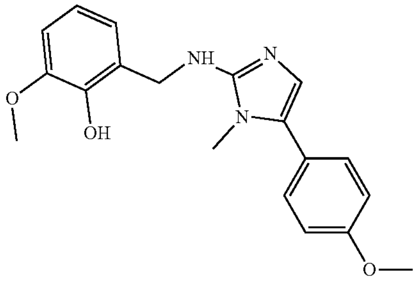

[Chemical Formula 1-2]

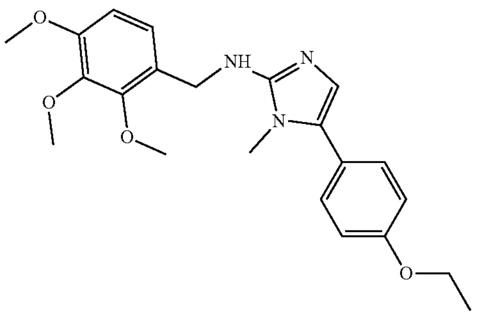

-continued

[Chemical Formula 1-3]

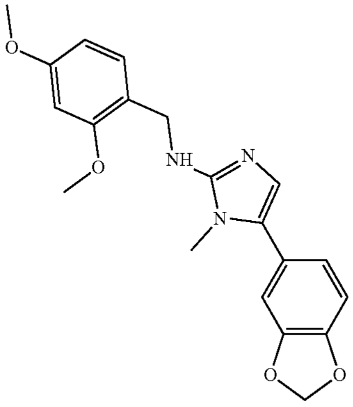

[Chemical Formula 1-4]

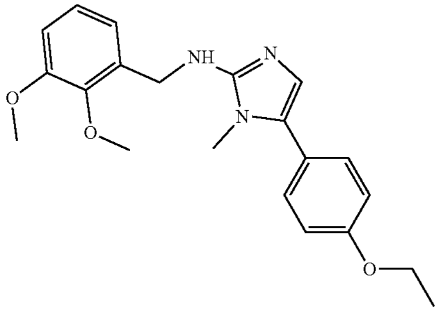

[Chemical Formula 1-5]

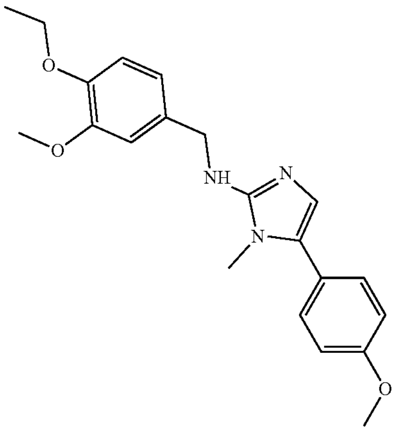

-continued

[Chemical Formula 1-6]

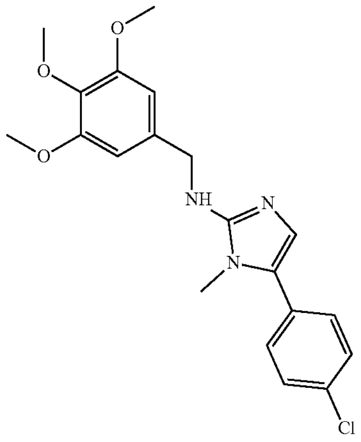

In the present specification, the compound of Chemical Formula 1-1 is named TIC10, the compound of Chemical Formula 1-2 is named TIC10-3, the compound of Chemical Formula 1-3 is named TIC10-7, the compound of Chemical Formula 1-4 is named TIC10-8, the compound of Chemical Formula 1-5 is named TIC10-10, and the compound of Chemical Formula 1-6 is named TIC10-11.

In the present invention, the compound exhibiting TLR inhibitory activity preferably has the structure represented by Chemical Formula 1-1 or Chemical Formula 1-3, but the present invention is not limited thereto.

In another aspect, the present invention is directed to a composition for inhibiting TLR (toll-like receptor) comprising the compound represented by Chemical Formula 1 or the pharmaceutically acceptable salt thereof.

As used herein, the term "inhibiting" or "inhibition" refers to a phenomenon by which biological activity or signaling activity is deteriorated due to deficiency, disharmony, or any of a large number of other causes, and may include partial or complete blocking, reduction or prevention of activity of TLR, delaying of activation, inactivation, or downregulation.

As used herein, the term "inhibitor" refers to a molecule that partially or completely inhibits the effect of another molecule, such as a receptor or intracellular mediator, by any mechanism.

In the present invention, the compound represented by Chemical Formula 1 is capable of inhibiting the signaling pathway of at least one TLR selected from the group consisting of TLR7, TLR9, TLR3, and TLR8. Preferably, the compound inhibits the signaling pathway of TLR7 and/or TLR9, but the present invention is not limited thereto.

In the present invention, "inhibition of the signaling pathway of TLR7, TLR9, TLR3, or TLR8" means directly or indirectly or substantially interfering with, reducing, or inhibiting the biological activity of TLR7, TLR9, TLR3, or TLR8, preferably inhibiting the activity of NF-κB and MAPK and reducing the secretion of inflammatory cytokines by blocking the signaling pathway of TLR7, TLR9, TLR3, or TLR8 due to binding to the TLR7, TLR9, TLR3, or TLR8 receptor and neutralization of the activity thereof.

In the present invention, the compound represented by Chemical Formula 1 may perform at least one selected from among inhibition of secretion of TNF-α (tumor necrosis factor-α), inhibition of activation of NF-κB (nuclear factor k-light-chain-enhancer of activated B cells), and inhibition of activation of MAPKs (mitogen-activated protein kinases).

As used herein, the term "TLR7" refers to a protein that belongs to the family of TLRs, which is a family of transmembrane proteins that function to monitor pathogen infection, and TLR7 is a protein encoded by the TLR7 gene and is also called UTNQ248/PRO285. TLR7 activates the innate immune system by recognizing ssRNA (single-stranded RNA) of RNA virus or synthetic small molecules such as imidazoquinoline, loxoribine, and bropirimine.

As used herein, the term "TLR9" refers to a protein that belongs to the family of TLRs, which is a family of transmembrane proteins that function to monitor pathogen infection, and TLR9 is a protein encoded by the TLR9 gene, and is also called CD289 or UTNQ5798/PRO19605. TLR9 activates the innate immune system by recognizing unmethylated CpG oligodeoxynucleotide DNA of bacteria or DNA viruses.

As used herein, the term "TLR3" refers to a protein that belongs to the family of TLRs, which is a family of transmembrane proteins that function to monitor pathogen infection, and TLR3 is a protein encoded by the TLR3 gene, and is also called CD283 or IIAE2. TLR3 is very important for the activation of the innate immune system because it recognizes double-stranded RNA (dsRNA) and poly I:C of the virus.

As used herein, the term "TLR8" refers to a protein that belongs to the family of TLRs, which is a family of transmembrane proteins that function to monitor pathogen infection, and TLR8 is a protein encoded by the TLR8 gene and is also called CD288 (cluster of differentiation 288) or UNQ249/PRO286. TLR8 is activated by single-stranded viral RNA, phagocytized bacterial RNA, or synthetic small-molecule TL8.

Specific inhibition of TLRs using novel chemicals or biological agents has been beneficial over the years to treat autoimmune/inflammatory, moderate-to-life threatening diseases in preclinical or clinical settings. However, since most TLRs recognize a variety of exogenous and endogenous ligands and trigger the production of proinflammatory cytokines through overlapping signaling pathways (Kawasaki T. & Kawai T. (2014) *Front Immunol.* 5:461), specific inhibition of a single TLR becomes inefficient to block simultaneous signaling cascades initiated by another cognate TLR. Due to the ability of endosomal TLRs to induce robust TNF-α or type I IFN expression in response to virus-, bacteria-, or host-derived nucleic acid fragments, endosomal TLRs (TLR7, TLR8 and TLR9) are commonly implicated in systemic inflammatory diseases such as SLE and RA. Therefore, the development of therapeutic agents to prevent the inappropriate activation of these TLRs has great potential and is a subject of intense research.

The present invention is intended to identify human TLR9-specific small-molecule antagonists through the in-silico virtual screening of large multiconformational chemical compound libraries. Based on the results of experimental validation of high-scoring virtual hit sets in cell-based bioassays, a compound, referred to as TIC10, exhibited not only stronger inhibition of TLR9, but also a moderate decrease in TLR7-mediated TNF-α production. Further evaluation of structural derivatives having modifications around the main scaffold of TIC10 demonstrated that an analogue, referred to as TIC10-7, significantly downregulated TLR7- and TLR9-mediated cytokine secretion in a concentration-dependent manner. These results support a previous report that multiple endosomal TLRs are capable of being regulated by a single therapeutic agonist/antagonist targeting a common ligand-binding pocket of the receptor (Jurk M., Heil F. et al. (2002) *Nat. Immunol.* 3(6):499).

In recent years, drug development programs have targeted TLR9 through computational or structure-activity relationship approaches. However, there are limitations thereon because the crystal structure of the TLR bound to the small-molecule modulator is unknown. The computational drug discovery principle largely depends on the accurate definition of active/binding sites on the receptor, failing which makes the interpretation of docking results difficult. Although alternative approaches, such as homology modeling or quantitative structure-activity relationship modeling (QSAR modeling) exist, the accuracy of these approaches is still a matter of debate (Sliwoski G. et al. (2014) *Pharmacol. Rev.* 66(1):334-395). Since the structure of human TLR9 has not yet been confirmed, the present inventors made a homology model based on the structure of horse TLR9 as a template. Two distinct ligand-binding sites were defined: site I overlaps the small-molecule binding site of TLR7, and site II binds to CpG DNA. Interestingly, the preliminary hit (TIC10) belongs to a docking round where site I is defined as a binding pocket, and TIC10-7, which is a potent analogue thereof, exhibits interactions not only with site I, but also with site Ia binding to the 5'-xCx DNA motif of TLR9 (Ohto U. et al. (2018) *Immunity* 48(4):649-658 e644). A recently discovered small molecule antagonist of TLR8 has been shown to target a location closer to, but distinct from, site I, and to stabilize the resting state of the receptor. Likewise, previous SAR studies have indicated that both agonists and antagonists exert immunomodulatory effects on TLR7 and TLR8 by competing for similar binding sites (Salunke D. B. et al. (2012) *J. Med. Chem.* 55(18): 8137-8151). Based on these facts, binding of TIC10 or TIC10-7 to site I/Ia of TLR7 or TLR9 appears to be very reasonable.

While the development of small molecule agonists targeting endosomal TLRs is well known, the development of antagonists is limited due to a lack of knowledge about the mechanism of receptor activation. Previous studies have suggested that ligand binding is required for receptor dimerization. However, according to recent structural data, TLR1/TLR2 heterodimers or TLR3, TLR8, and TLR9 homodimers exist as preformed loose dimers in a so-called "resting state". Ligand recognition promotes conformational alterations, thus causing the formation of a high-affinity receptor-adaptor complex in the cytosol. Thus, stabilizing the resting (or inactive) state using an allosteric modulator may be an efficient strategy to simultaneously target TLR family members. The allosteric sites may be distinguished from typical agonist binding sites, but the inhibitors that interact with agonists may interfere with agonist recognition and prevent conformational changes required for adaptor recruitment. In addition to direct inhibitors, several imidazoquinolines, such as antimalarial drugs (chloroquine and hydroxychloroquine), are known to block activation of endosomal TLRs through alternative mechanisms (Kuznik A. et al. (2011) *J Immunol.* 186(8):4794-4804). These drugs blunt the immunostimulatory effects of CpG DNA, RNA, and immune complexes at very low concentrations. According to mechanistic studies, chloroquine and hydroxychloroquine exhibit strong affinity for CpG DNA or other nucleic acid-immune complexes, thus blocking the availability thereof to TLR binding sites. Therefore, both direct and indirect antagonists of TLR7/TLR8/TLR9 have great prospects in the treatment of autoimmune diseases (e.g. SLE and RA).

In summary, in the present invention, TIC10, which is a TLR9-specific inhibitor, and TIC10-7, which is a potent TLR7/TLR9 dual inhibitor, were identified using computational drug discovery approaches, and cell-based assays demonstrated that TIC10-7 prevented the expression of TNF-α in RAW 264.7 cells by obstructing the activation of NF-κB and MAPK. According to computational modeling and as reported in the literature, ligands have high binding potential to site I of TLR7 or site I/Ia of TLR9 extracellular domain. Consequently, TIC10-7 is capable of being used as a novel chemical probe to elucidate the biological relevance of TLR7 and TLR9 to autoimmune disease models, and is able to serve as a lead material for therapeutic development.

In an embodiment of the present invention, the compound of Chemical Formula 1-1 or Chemical Formula 1-3 according to the present invention is very effective at inhibiting the activation of NF-κB and MAPKs by inhibiting the TLR7 and/or TLR9 signaling pathway, and is thus efficiently utilized for a composition for preventing or treating an autoimmune disease and an inflammatory disease caused by TLR7 or TLR9 signaling pathways.

Accordingly, still another aspect, the present invention is directed to a composition for preventing or treating an autoimmune disease comprising the compound or the composition for inhibiting TLR (toll-like receptor).

Yet another aspect, the present invention is directed to a composition for preventing or treating an inflammatory disease comprising the compound or the composition for inhibiting TLR (toll-like receptor).

As used herein, the term "autoimmune disease" refers to a disease that is caused by a process in which a problem occurs in establishing or maintaining self-tolerance, resulting in an immune response to a self-antigen, thereby attacking one's own tissues. Here, "self-tolerance" refers to immunologic unresponsiveness that does not cause harmful reactions to antigenic substances constituting the self. The autoimmune disease of the present invention is selected from the group consisting of systemic lupus erythematosus, psoriasis, psoriatic arthritis, rheumatoid arthritis, experimental autoimmune arthritis, asthma, Crohn's disease, multiple sclerosis, experimental autoimmune encephalomyelitis, myasthenia gravis, thyroiditis, experimental forms of uveitis, Hashimoto's thyroiditis, primary myxedema, thyrotoxicosis, pernicious anemia, autoimmune atrophic gastritis, Addison's disease, premature menopause, male infertility, childhood diabetes, Goodpasture's syndrome, pemphigus vulgaris, pemphigoid, sympathetic ophthalmitis, lens-induced uveitis, autoimmune hemolytic anemia, idiopathic leukopenia, primary sclerosing cholangitis, chronic active hepatitis, latent cirrhosis, ulcerative colitis, Sjogren's syndrome, scleroderma, Wegener's granulomatosis, polymyositis, dermatomyositis, and discoid lupus, but is not limited thereto.

As used herein, the term "inflammatory disease" refers to a disease that is caused by an inflammatory material (inflammatory cytokine) such as TNF-α, IL-1, IL-6, prostaglandin, leukotriene, or NO secreted from immune cells such as macrophages due to excessive stimulation of the immune system by harmful stimuli such as inflammatory factors or radiation. The inflammatory disease of the present invention is selected from the group consisting of insulin-dependent diabetes mellitus, eczema, allergies, atopic dermatitis, acne, atopic rhinitis, pulmonary inflammation, allergic dermatitis, chronic sinusitis, contact dermatitis, seborrheic dermatitis, gastritis, gout, gouty arthritis, ulcers, chronic bronchitis, ulcerative colitis, ankylosing spondylitis, sepsis, angiitis, bursitis, temporal arteritis, solid cancers, Alzheimer's disease, arteriosclerosis, obesity, and viral infection, but is not limited thereto.

The composition for preventing or treating an autoimmune disease or inflammatory disease according to the present invention may comprise the compound alone in a pharmaceutically effective amount, or may comprise at least one pharmaceutically acceptable carrier, excipient, or diluent. Here, the pharmaceutically effective amount is an amount sufficient to prevent, ameliorate and treat symptoms of the autoimmune disease or inflammatory disease.

"Pharmaceutically acceptable" means that a material is physiologically acceptable and does not usually cause allergic reactions such as gastrointestinal disorders and dizziness or reactions similar thereto when administered to humans. Examples of the carrier, excipient, or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oil. In addition, fillers, anti-aggregation agents, lubricants, wetting agents, fragrances, emulsifiers, and preservatives may be further included.

In addition, the composition for preventing or treating the disease according to the present invention may comprise at least one known active ingredient having a therapeutic effect on an autoimmune disease or inflammatory disease, in addition to the compound or the pharmaceutically acceptable salt thereof.

The composition for preventing or treating the disease according to the present invention may be formulated using methods known in the art so as to provide rapid, sustained, or delayed release of an active ingredient after administration to a mammal other than a human. Formulations may take the form of powders, granules, tablets, emulsions, syrups, aerosols, soft or hard gelatin capsules, sterile injectable solutions, or sterile powders.

The composition for preventing or treating the disease according to the present invention may be administered through various routes including oral, transdermal, subcutaneous, intravenous, or intramuscular routes, and the dosage of the active ingredient may be appropriately selected depending on various factors such as the route of administration, the age, gender, and body weight of the patient, the severity of disease, etc., and the composition may be administered in combination with a known compound having an effect of preventing, ameliorating or treating symptoms of autoimmune diseases or inflammatory diseases.

Still yet another aspect, the present invention is directed to a method of preventing or treating an autoimmune disease comprising administering the compound or the composition for inhibiting TLR.

A further aspect, the present invention is directed to the use of the compound or the composition for inhibiting TLR for the prevention or treatment of an autoimmune disease.

Still a further aspect, the present invention is directed to the use of the compound or the composition for inhibiting TLR for the manufacture of a medicament for the prevention or treatment of an autoimmune disease.

Yet a further aspect, the present invention is directed to a method of preventing or treating an inflammatory disease comprising administering the compound or the composition for inhibiting TLR.

Still yet a further aspect, the present invention is directed to the use of the compound or the composition for inhibiting TLR for the prevention or treatment of an inflammatory disease.

Even yet a further aspect, the present invention is directed to the use of the compound or the composition for inhibiting TLR for the manufacture of a medicament for the prevention or treatment of an inflammatory disease.

Since the above-described "compound or composition for inhibiting TLR" is employed in the prevention or treatment method and the use according to the present invention, redundant descriptions thereof will be omitted.

A better understanding of the present invention may be obtained through the following examples. These examples are merely set forth to illustrate the present invention, and are not to be construed as limiting the scope of the present invention, as will be apparent to those of ordinary skill in the art.

Example 1: Materials and Methods

Example 1-1: Cell Lines and Reagents

A murine macrophage cell line (RAW 264.7) was obtained from the Korean Cell Line Bank (KCLB) and the Korean Cell Line Research Foundation (KCLRF). The cells were cultured in DMEM (Dulbecco's modified Eagle's medium; HyClone Laboratories, Inc., San Angelo, Texas, USA) supplemented with 1% penicillin/streptomycin (HyClone Laboratories, Inc.) antibiotic mixture and 10% fetal bovine serum (FBS; Thermo Fisher Scientific, Inc., Waltham, MA, USA). A human monocytic cell line (THP-1) was provided by Dr. Chang-Hee Suh, Ajou University School of Medicine, Suwon, Korea. The cells were cultured in RPMI 1640 (HyClone Laboratories, Inc.) and t differentiated into macrophages by applying 80 nM phorbol 12-myristate 13-acetate (PMA; Sigma-Aldrich Co., St. Louis, MO, USA) for 48 h. All cell lines were maintained in a humidified incubator (37° C., 5% $CO_2$), and the medium was replaced after overnight incubation.

Agonists specific to TLR1/TLR2 (Pam3CSK4), TLR2/TLR6 (FSL-1), TLR3 (Poly I:C), TLR7 (imiquimod), and TLR8 (TL8-506) were purchased from InvivoGen Ltd. (Hong-Kong, China), and a TLR4-specific agonist (LPS from *E. coli* O111:B4) was purchased from Sigma-Aldrich, Inc. For TLR9-specific stimulation, class C CpG-ODN (ODN2395, 5'-TCG TCG TTT TCG GCG CGC GCC G-3') having full phosphorothioate backbone modification was synthesized (Bioneer, Inc., Daejeon, Korea). All TLR agonists were dissolved in deionized water and applied to a culture media for TLR activation. The cells were treated with test compounds or a control medium for 1 hour, and then stimulated with a TLR agonist for 4 hours, or 24 hours in the case of poly(I:C), and the cytokine secretion was monitored.

Example 1-2: Analysis of Cell Viability

RAW 264.7 cells were seeded onto 96-well cell culture plate at a density of $2\times10^4$ cells/well and allowed to stabilize overnight. The cells were treated with test compounds or a negative control (DMSO; dimethyl sulfoxide) for 24 hours, where the final DMSO concentration of the treated well was 0.25%. Then, the medium was removed, and 500 μg/ml of an MTT (3-(4,5-dimethylthiazol-2-yl)-2,5-diphenyltetrazolium bromide, InvivoGen Ltd.) solution was added to each well. After 3 hours, the solution was replaced with DMSO (Biosesang Co. Ltd., Korea), and incubated for an additional 30 minutes to complete formazan dissolution. Absorbance was measured by a microplate colorimetric reader at a wavelength of 595 nm and normalized to the control for the determination of the cell viability. All incubations were performed under the same conditions as described above.

Example 1-3: ELISA

RAW 264.7 or differentiated THP-1 cell lines were seeded onto a 96-well culture plate at a density of $2\times10^4$ cells/well. The cells were treated with test compounds for 1 hour followed by the stimulation with TLR agonists for 4 hours. The supernatant was transferred to pre-coated assay plates, and the secretion levels of mouse and human TNF-α were measured by respective ELISA kits (Invitrogen, Carlsbad, CA, USA). All experiments were performed according to the manufacturer's instructions. Absorbance was measured by a microplate reader spectrophotometer (Molecular Devices, Inc., San Jose, CA, USA), and data was interpolated from a standard curve using SoftMax Pro 5.3 software (Molecular Devices, Inc.).

Example 1-4: Immunoblotting

RAW 264.7 cells were seeded into a 60 mm cell culture dish at a density of $2\times10^6$ cells/dish, and treated with test compounds followed by TLR agonists. The cell lysate was harvested through mammalian protein extraction kit (M-PER; Thermo Fisher Scientific, Inc.) with the protease and phosphatase inhibitor cocktail (Thermo Fisher Scientific, Inc.), and the protein levels were quantified using a bicinchoninic acid assay (Sigma-Aldrich, Co.). Protein samples were separated by SDS-PAGE and transferred to nitrocellulose membranes (GE Healthcare, Inc., Chicago, IL, USA). The membranes were incubated with primary antibodies specific to phospho-JNK (Cell Signaling Technology, Inc., Danvers, MA, USA), phospho-ERK (Santa Cruz Biotechnology, Inc., Dallas, TX, USA), phospho-p38-MAPK (Cell Signaling Technology, Inc.), phospho-p65 (Cell Signaling Technology, Inc.), or β-actin (Santa Cruz Biotechnology, Inc.). Proteins were proved by means of HRP-conjugated anti-rabbit IgG or anti-mouse IgG (Thermo Fisher Scientific, Inc.) antibody. Protein levels were confirmed using a chemiluminescent substrate (SuperSignal™ West Pico PLUS, Thermo Fisher Scientific, Inc.) and a luminescence detection system (Fusion Solo S, VILBER, France).

Example 1-5: Construction of Virtual Screening Library

A multiconformational screening library was prepared by combining the chemical structures obtained from ZINC database (druglike and leadlike) (Irwin J. J. et al. (2012) *J. Chem. Inf Model* 52(7):1757-1768) as well as from different commercial vendors (Table 1). Ligand libraries are freely available from the ZINC database (https://zinc.docking.org/).

TABLE 1

Chemical compound libraries used for the ligand screening

| Compound library | Number of compounds |
|---|---|
| ZINC druglike | 14,480,911 |
| ZINC leadlike | 5,449,805 |
| Enamine | 3,006,354 |
| ChemBridge | 1,591,767 |

TABLE 1-continued

| Chemical compound libraries used for the ligand screening | |
|---|---|
| Compound library | Number of compounds |
| ChemDiv | 1,960,042 |
| Life Chemicals | 500,011 |
| Maybridge | 72,257 |
| Total | 27,061,147 |

The structures were cleaned up using the sdwash tool of Molecular Operating Environment (MOE) software (Molecular Operating Environment (MOE), 2013.08; Chemical Computing Group ULC, 1010 Sherbooke St. West, Suite #910, Montreal, QC, Canada, H3A 2R7, 2017). Briefly, disconnected salt molecules and inorganic metal ions were removed from the structures. Ligands having reactive groups were removed, and the largest fragment of the broken ligand was retained in the library. An explicit hydrogen atom was added, and the protonation state was adjusted to pH 7.0. A maximum of 10 tautomeric states were enumerated for each ligand, and intramolecular bonds were scaled to the appropriate length. Then, the chemical library was subjected to energy minimization using the MMFF94x force field until a root mean square gradient of 0.1 was reached. The partial charge of the ligand was calculated with the MMFF94x force field before energy minimization.

Example 1-6: Calculation of Molecular Fingerprints and Similarity Search

Unique molecular fingerprints were assigned to ligands in the screening library based on the bit-packed MACCS Structural Keys (FP:BIT_MACCS) scheme. An in-house support vector language (SVL) script of MOE was applied to identify the chemical structures having at least 60-80% similarity to a selected set of TLR9 antagonists (Table 2).

TABLE 2

List of ligands used for fingerprint-based similarity searches against multiconformational compound library

| Inhibitor name | Target | Activity (μM) | Reference |
|---|---|---|---|
| CHEMBL457704 | TLR9 | $IC_{50}$ = 0.02 | Lipford G. et al. (2008) |
| CHEMBL515364 | TLR9 | $IC_{50}$ = 0.03 | Small-Molecule Inhibitors of Toll-like Receptor 9. U.S. Pat. No. 7,410,975B2 |
| CPG-52364 | TLR9 | $IC_{50}$ = 0.0046 | Watanabe M. et al. |
| Compound 18 | TLR9 | $IC_{50}$ = 0.013 | (2014) *ACS Med. Chem. Lett.* 5(11): 1235-1239 |
| T5669070 | TLR9 | $IC_{50}$ = 0.0534 | Zatsepin M. et al. |
| T5581953 | TLR9 | $IC_{50}$ = 0.201 | (2016) *J. Chem. Inf. Model* 56(9): |
| T5570245 | TLR9 | $IC_{50}$ = 0.815 | 1835-1846 |
| T6683896 | TLR9 | $IC_{50}$ = 0.896 | |
| T5428933 | TLR9 | $IC_{50}$ = 0.962 | |

TLR9; Ligand names were used as mentioned in their respective literature/patent/database identification identifiers.

Similarity searches were performed by using a Tanimoto similarity metric, called the Tanimoto coefficient. The similarity metric is based on the following formula #AB/(#A+#B−#AB). Here, A and B are two molecular fingerprints, and #indicates the number of features in each fingerprint. The resultant ligands were saved in a separate library for further screening.

Example 1-7: Preparation of Receptor Structures

The crystal structures of horse TLR9 (PDB ID: 3WPC) and monkey TLR7 (PDB ID: 5GMF) were obtained from PDB. Unnecessary ligands present in the crystal structure, including bound nucleic acids, were removed. The tertiary models of human TLR7 and TLR9 were constructed through homology modeling using the respective 5GMF and 3WPC templates in a SWISS MODEL web server (Waterhouse A. et al. (2018)*Nucleic Acids Res.* 46(W1):W296-W303). The obtained models were protonated at pH 7.0 and energy minimized using the Amber12:EHT force field until a root mean square gradient of 0.01 was reached.

Example 1-8: Molecular Docking of Ligand

The probable interactions between the known ligands (Table 2) and TLR9 were calculated through separate molecular dockings considering site I (F343, Y345, S350, F375, F402, D534*, Y536*, G563*, G565*) that corresponds to the small molecule binding cavity of TLR7 (Zhang Z. et al. (2016) *Immunity* 45(4):737-748), and site II (W47, F49, K51, S72, R74, H76, H77, W96, P99, S104, P105, M106, F108) that corresponds to the CpG DNA binding site of TLR9 (Ohto U. et al. (2015) *Nature* 520(7549):702-705). The docking was performed by employing the triangle matcher placement method and the London dG scoring function. The ligand poses were rescored using the MMFF94x force field and the GBVI/WSA dG scoring function. The docked poses were ranked based on the binding affinity thereof, i.e., the S-score.

Example 1-9: Pharmacophore Model Generation and Ligand-Based Screening

For each ligand shown in Table 2, different pharmacophore models were generated based on their best-ranking interactions with either site I or site II of TLR9. Pharmacophore features were assigned using the Planar-Polar-Charged-Hydrophobic scheme around the important ligand groups. Ligand-based virtual screening was then performed in order to identify structures that satisfy the essential pharmacophore constraints applied on each ligand. The resultant hits were combined into a single library and subjected to structure-based virtual screening through molecular docking.

Example 1-10: Structure-Based Virtual Screening

Virtual screening of the compound library obtained through pharmacophore screening was performed on each of site I and site II of TLR9. Screening was performed using the same parameters as described in Example 1-8 above. During docking calculations, the residues of TLR9 were kept rigid, but the ligand remained flexible. For each ligand, at least 10 different docked poses were saved and ranked on the basis of their S-score. Each docking round was repeated with an induced-fit docking method, and all of the ligand and receptor side chains adjusted the conformation thereof to obtain the best fit. The 16 highest-scoring consensus ligands obtained from both rigid and induced-fit docking rounds were selected for experimental validation of TLR9 antagonistic activity.

Example 1-11: Search for Potent Chemical Derivatives from Initial Lead

The structural derivatives of the initial lead, TIC10, were obtained from the MolPort database. A total of 100 ligands were downloaded as SDF files and converted to PDB format using MOE software. The ligands were washed and energy minimized with the same protocol used to prepare the initial screening library mentioned above. Molecular docking was performed on site I, which is the original binding site of TIC10, as well as on an additional site (site Ia: D259, Y345, R348, S350, A352, F375, R377, F402, D534*, Y536*, G565*, N567*) that was reported to bind to short synthetic DNA. Derivatives were docked and ranked based on the potential fit into site I and site Ia of TLR9 as well as into site I of TLR7 using the same docking parameters as mentioned in Example 1-8 above. For experimental validation of the antagonistic action thereof, 12 ligands having the highest scores in the three dockings were selected.

Example 1-12: Statistical Analysis

Statistical analysis was performed using a two-tailed paired Student's t-test in the Microsoft Excel software. The $IC_{50}$ calculation was performed using the GraphPad Prism program.

Example 2: Identification of Potent Lead TIC10 from the Virtual Screening

Figure 2A:
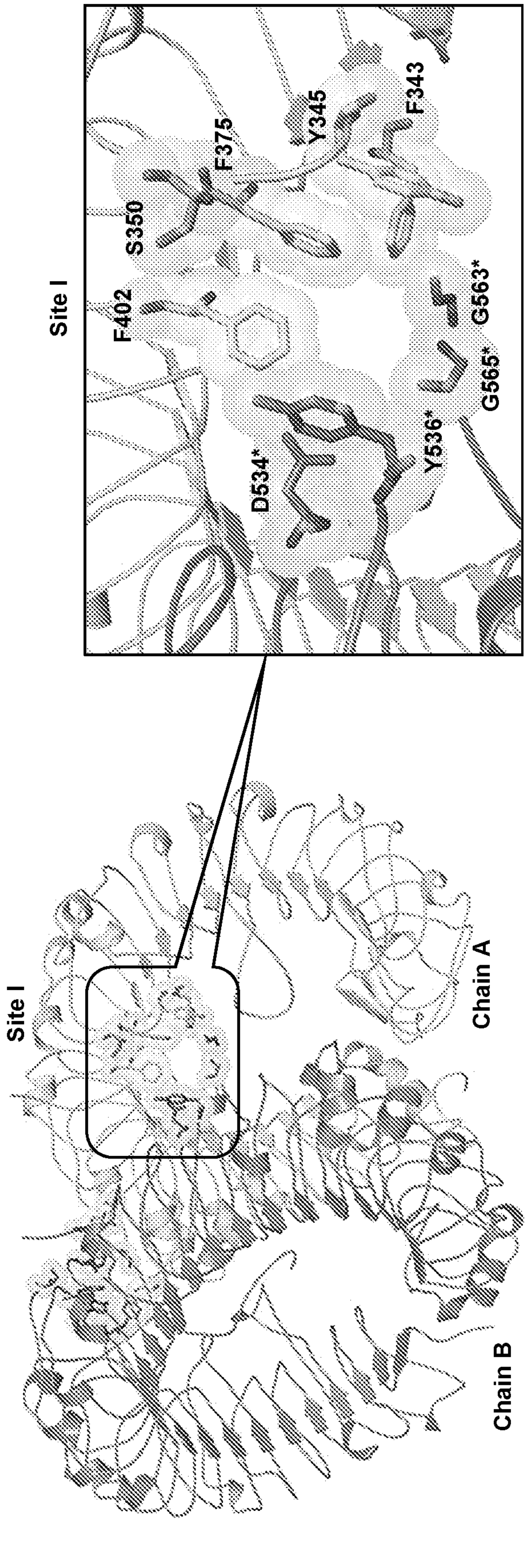
Figure 2B:
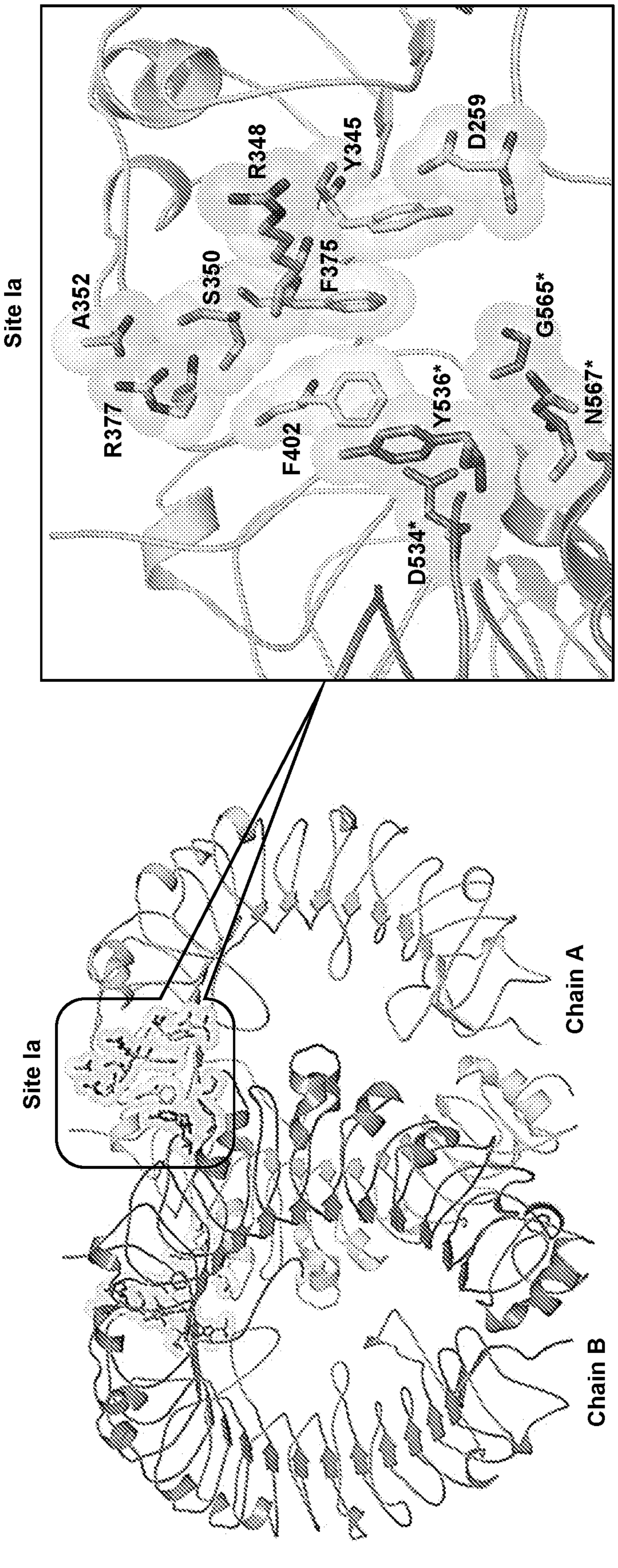
Figure 2C:
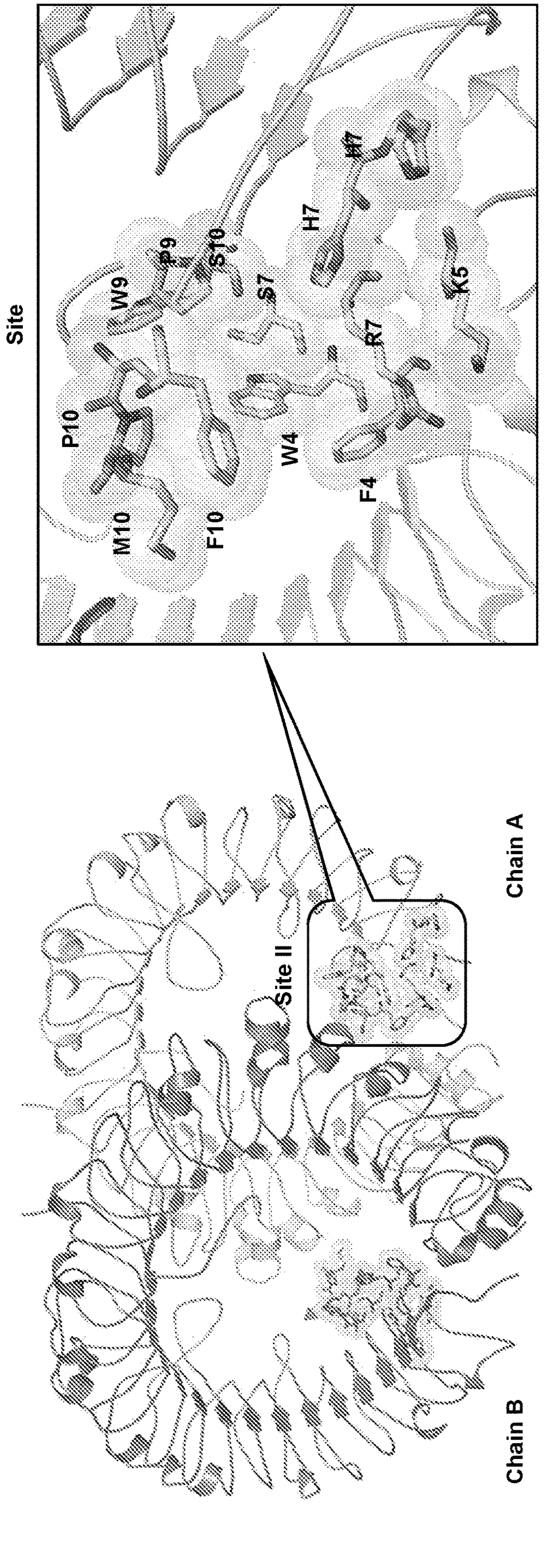

Experimental structures of TLR9 bound to small molecule ligands are not available in the protein data bank (PDB). The superimposition of the homology model of human TLR9 on the crystal structure of monkey TLR7 (PDB ID: 5GMF) indicated that the ligand-binding sites on both receptors overlap each other. Initially, in order to identify small molecule antagonists of TLR9, computer-aided virtual screening workflow was performed using the TLR9 homology model and a library of over 27 million commercially available chemical compounds (FIG. 1 and Table 1). After close visual inspection of about 100 high-ranking virtual hits obtained through multiple dockings so as to be potentially fit into the ligand-binding pocket of TLR9 (FIGS. 2A-2C), the 16 top-scoring consensus ligands (referred to as TIC1 to TIC16) were experimentally validated to assess the inhibitory activity thereof.

Figure 3A:
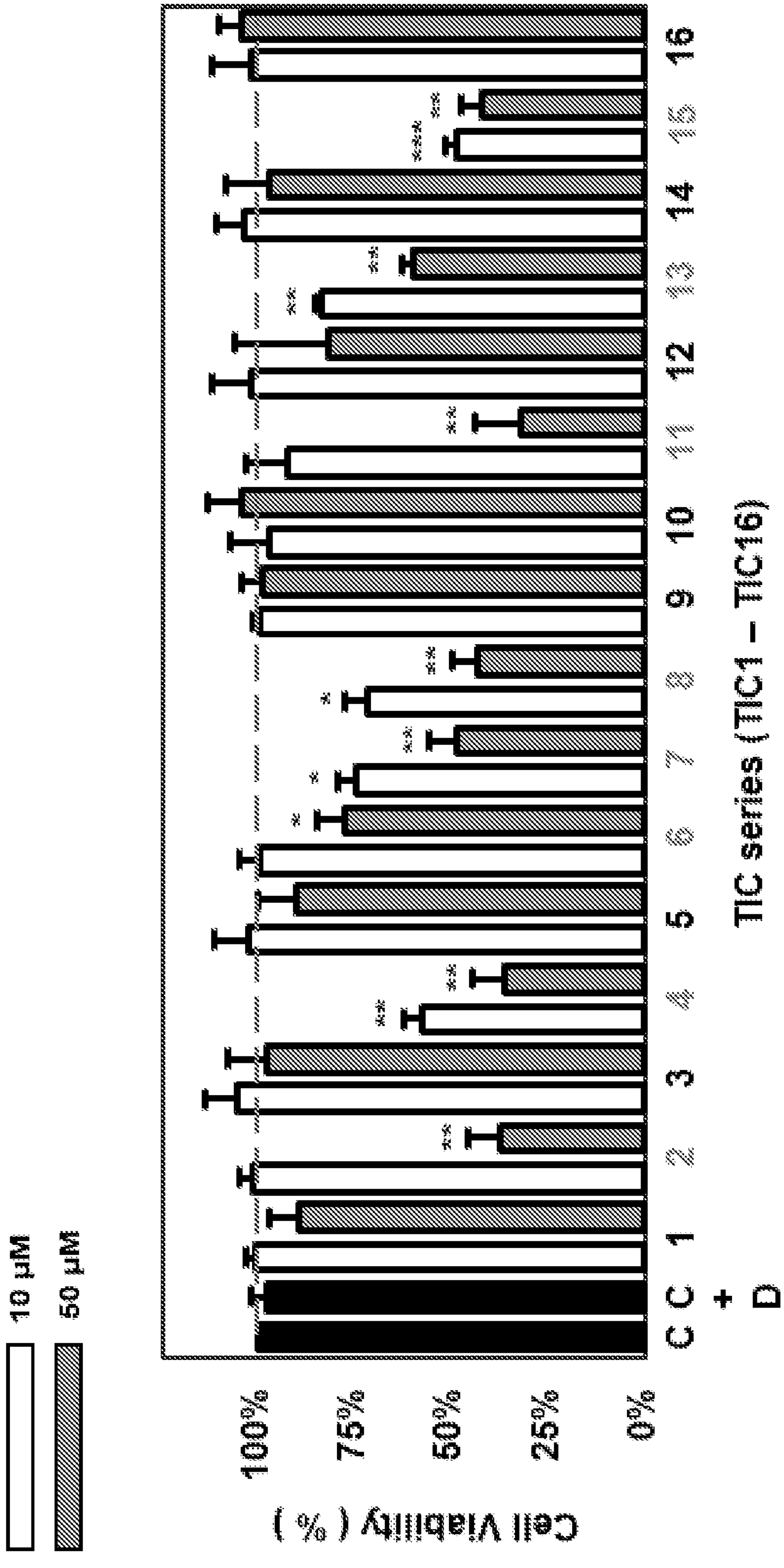
Figure 3B:
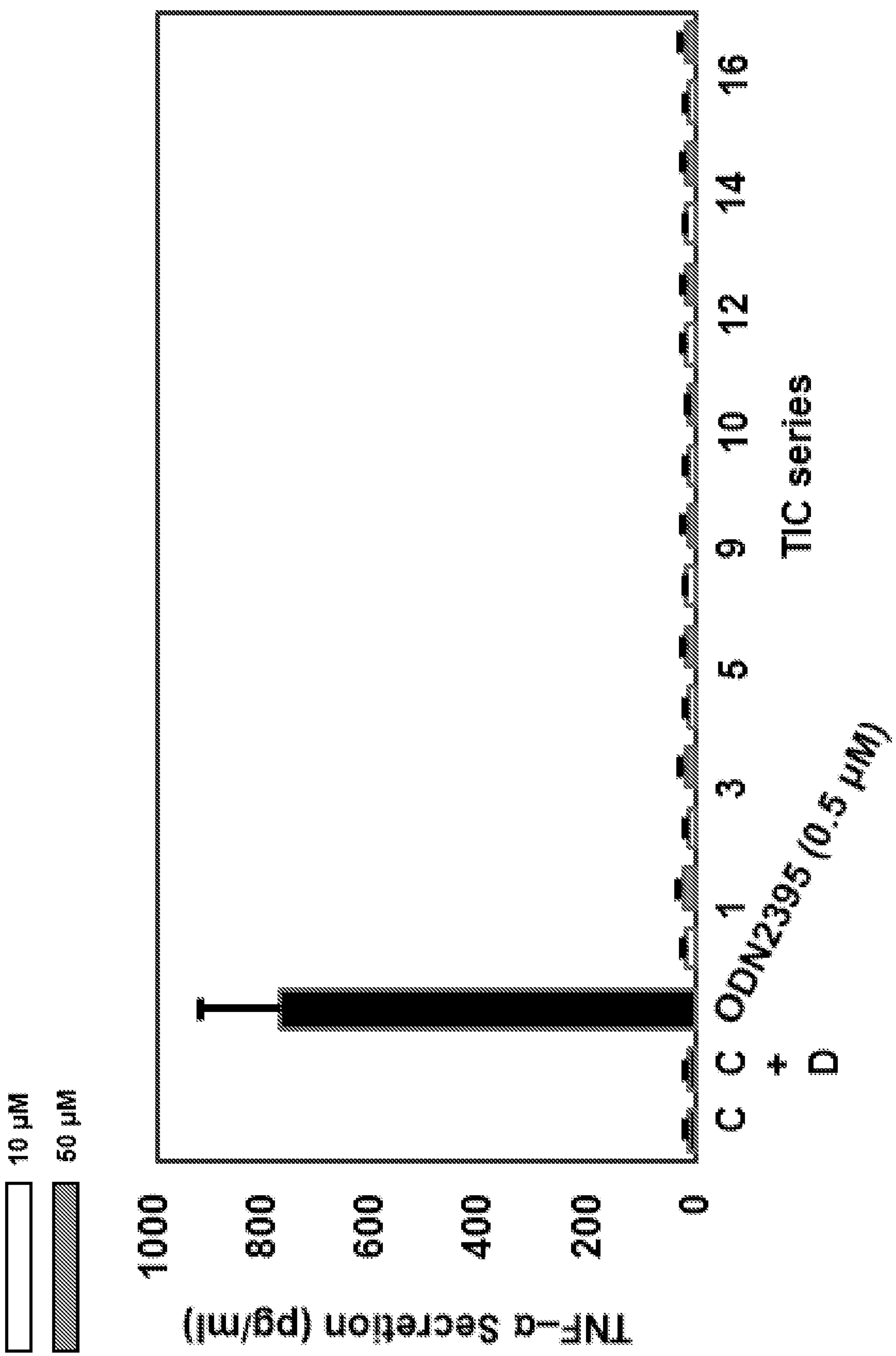

Before testing the antagonistic properties of the selected compounds, an MTT (3-(4,5-dimethylthiazol-2-yl)-2,5-diphenyltetrazolium bromide) assay was performed, whereby the cytotoxicity of the compounds in a murine macrophage cell line (RAW 264.7) was monitored. Among the 16 compounds, eight compounds (TIC1, TIC3, TIC5, TIC9, TIC10, TIC12, TIC14, and TIC16) were shown to be non-toxic or marginally toxic at a concentration of 50 μM (FIG. 3A). The other ligands were excluded as test subjects due to the high cytotoxicity thereof. Stimulation of RAW 264.7 cells with the above eight ligands (TIC1, TIC3, TIC5, TIC9, TIC10, TIC12, TIC14, and TIC16) did not induce the expression of proinflammatory cytokine TNF-α, negating a possible agonistic role in immune signaling pathways (FIG. 3B).

Figure 3C:
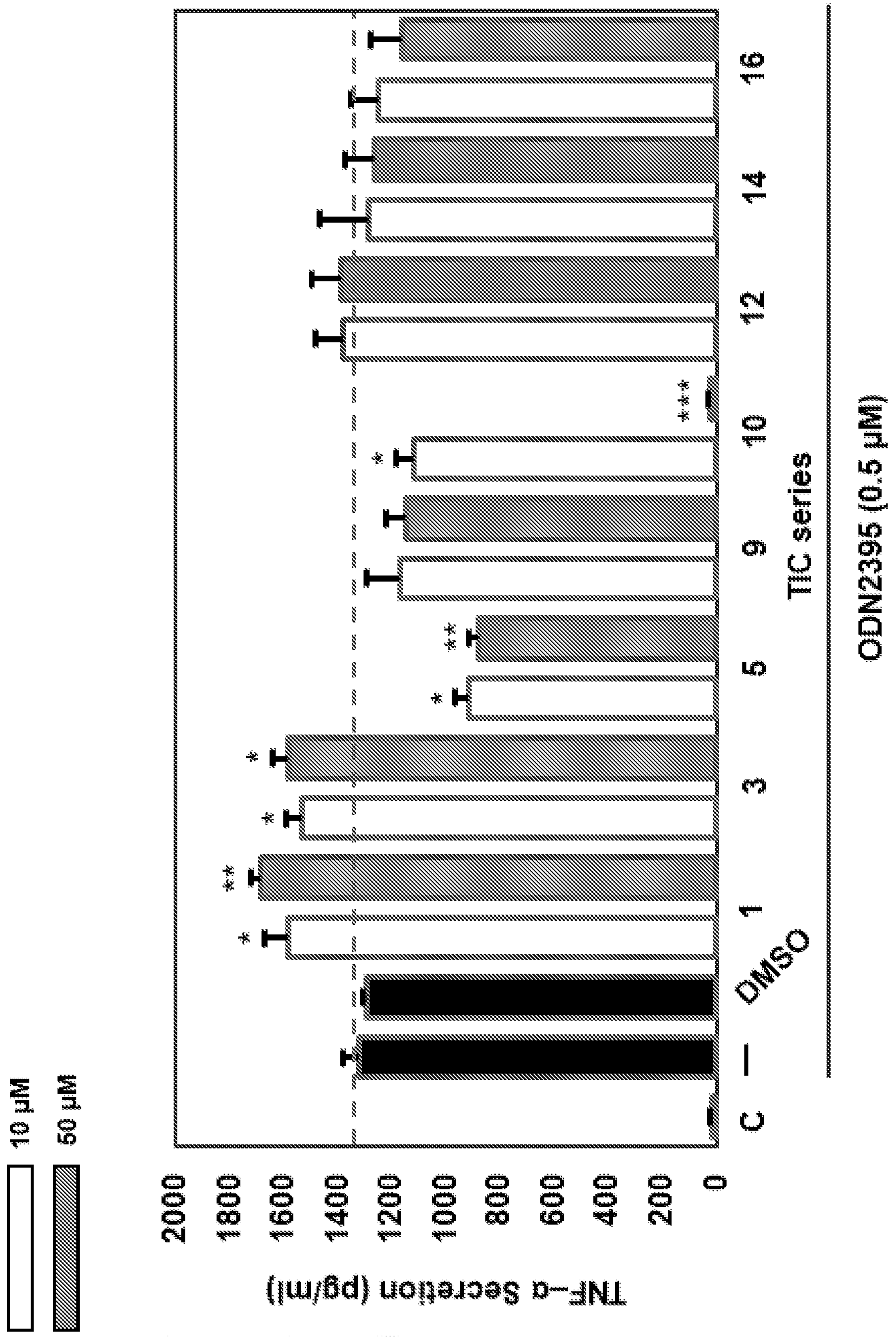
Figure 3D:
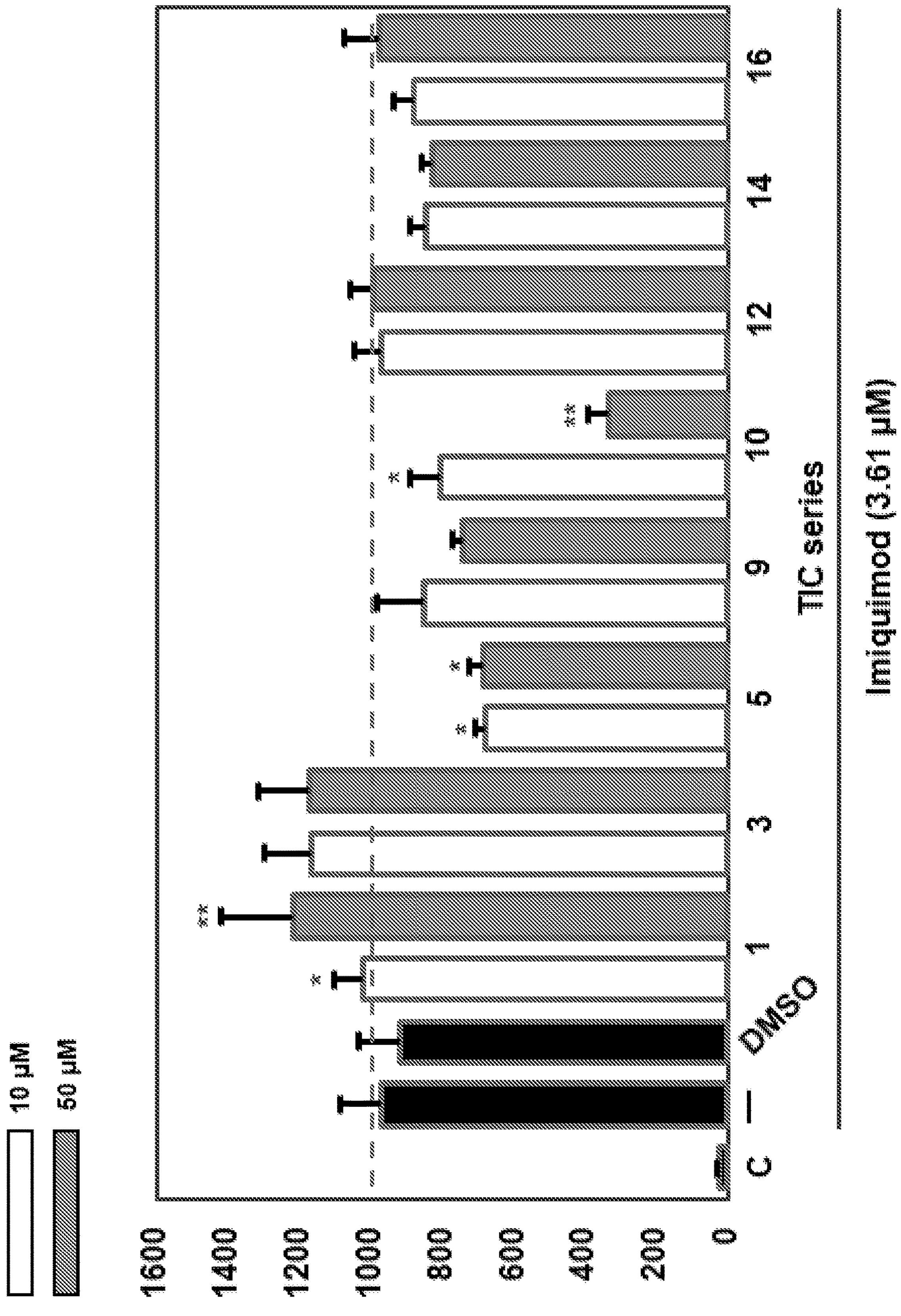

In order to evaluate the antagonistic effect of each compound on TLR7/TLR9 through ELISA (enzyme-linked immunosorbent assay), RAW 264.7 cells were pretreated with the eight compounds followed by the stimulation with a TLR7-specific agonist (imiquimod, 3.61 μM) or with a TLR9-specific agonist (ODN2395, 0.5 μM). Of the compounds screened, only TIC10 appeared to significantly inhibit TLR9-mediated TNF-α secretion at 50 μM (FIG. 3C). TIC10 also inhibited TLR7-mediated TNF-α secretion at 50 M (FIG. 3D), but to a lower extent than was observed for TLR9. Intriguingly, co-treatment with the TIC1 or TIC3 agonist slightly elevated cytokine production compared to the use of the agonist alone (FIG. 3C). Since the two ligands had no agonistic effect per se (FIG. 3B), the increased cytokine production may be due to cell activation (or non-specific cellular stress) by co-treatment. Consequently, TIC10 was selected as the most suitable lead for further optimization to improve the inhibitory potency against both TLR7 and TLR9.

Example 3: TIC10-7 Showing Greater Potency Against TLR7 and TLR9 Signaling

The improvement of the dual inhibitory effect of the primary lead TIC10 ($C_{19}H_{21}N_3O_3$) selected in Example 2 on the TLR7- and TLR9-mediated signaling pathways was sought through structural modification of the compound. A search for the commercially available derivatives of TIC in the MolPort database (https://www.molport.com/shop/index) suggested 100 distinct structures having various functional groups attached to the parent scaffold of TIC10. The derivatives were computationally docked into the ligand binding sites of TLR7 and TLR9 using the docked pose of TIC10 as a template and ranked based on the binding affinity score. The top 12 derivatives (hereinafter, referred to as TIC10-1 to TIC10-12) that scored better than TIC10 were selected, and the TLR7/TLR9-blocking abilities thereof were evaluated through ELISA.

Figure 4A:
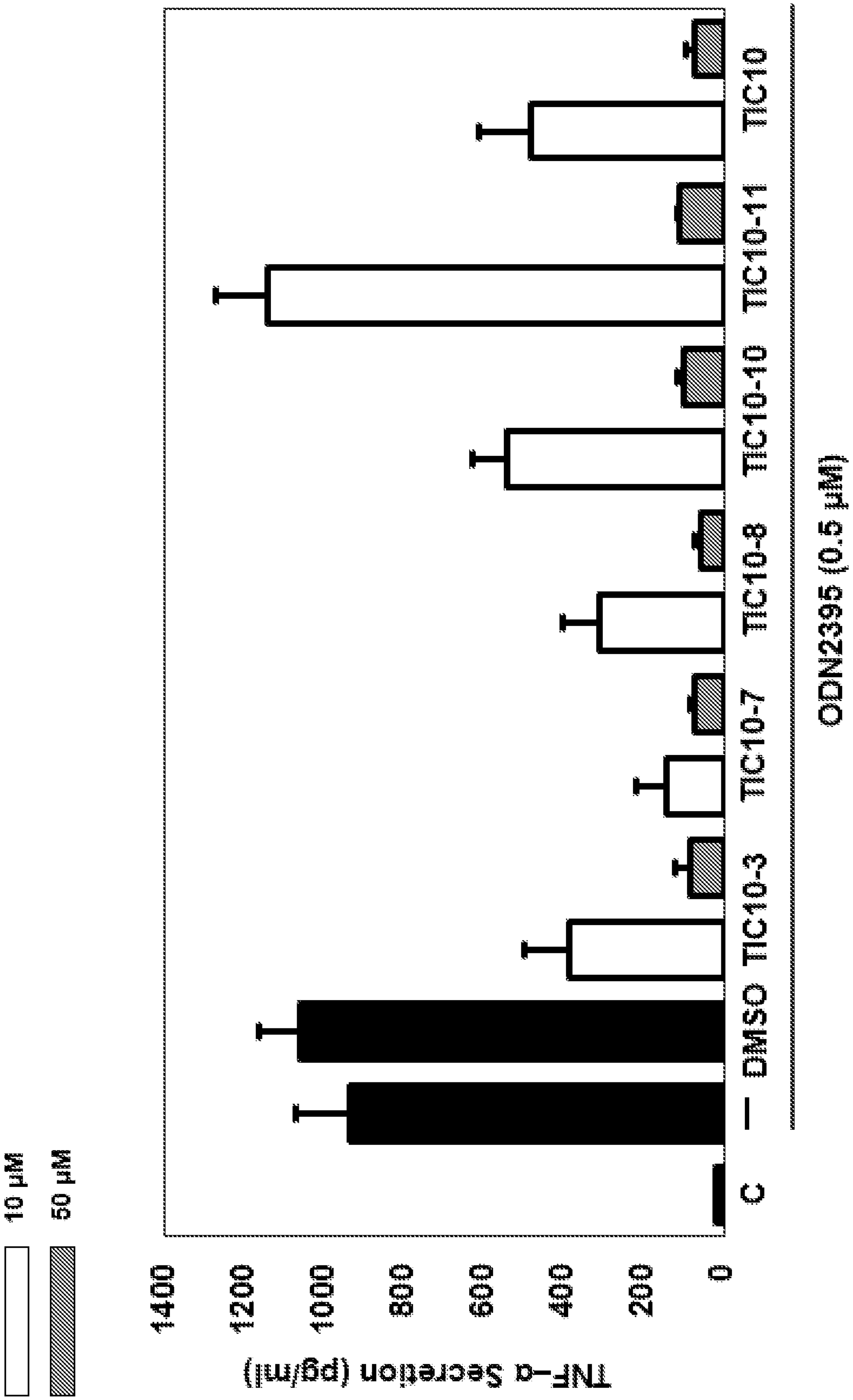
Figure 4B:
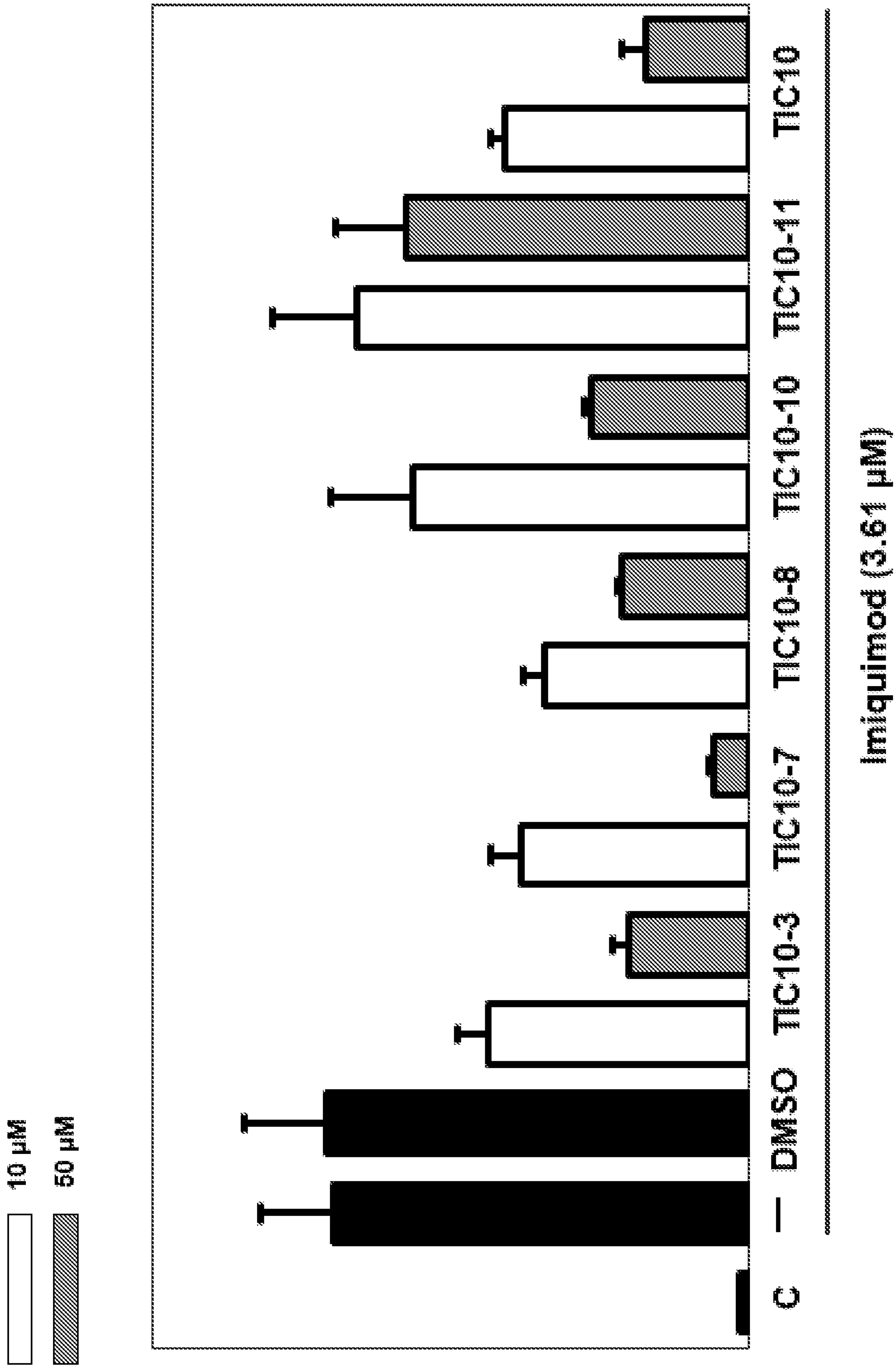
Figure 4C:
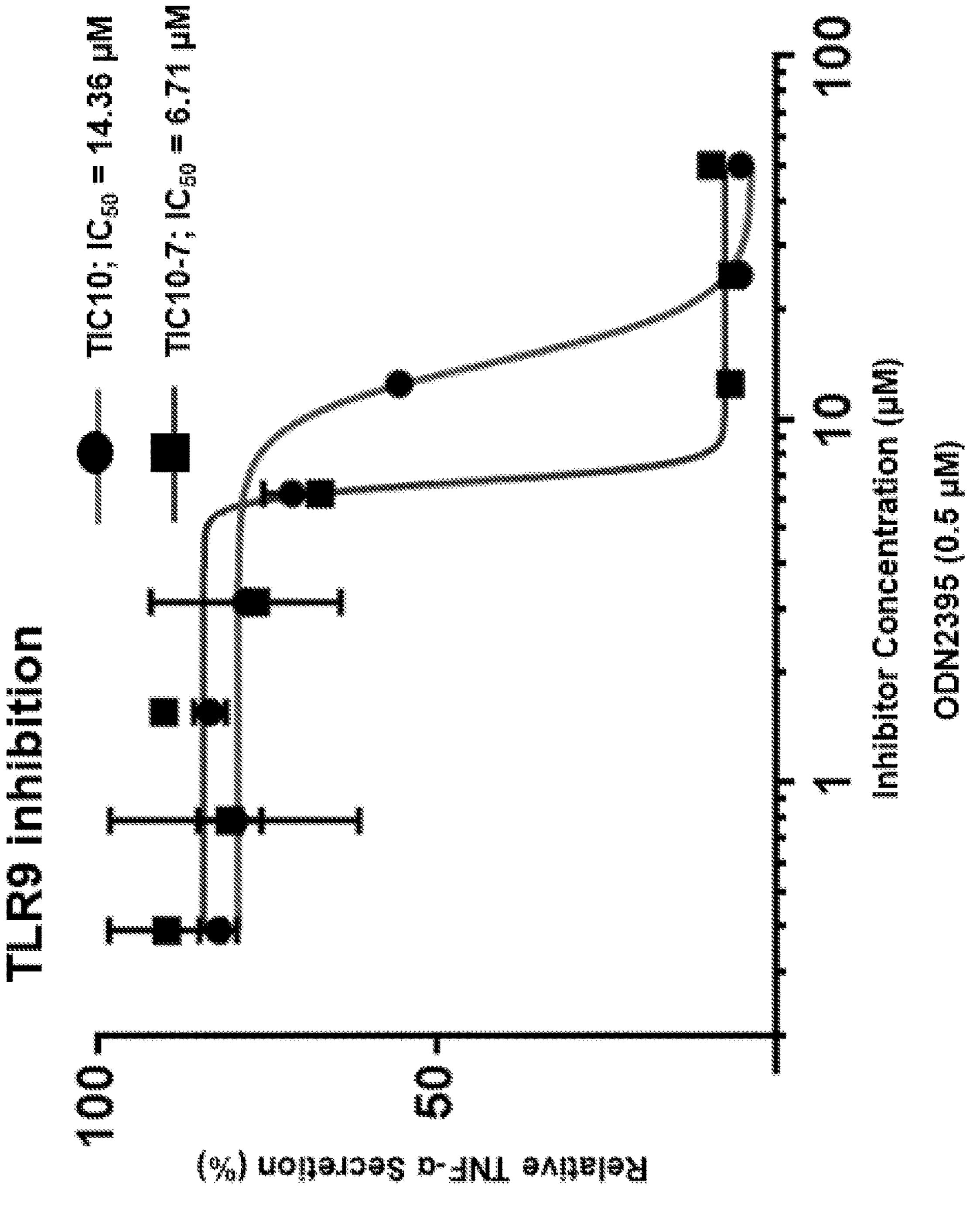
Figure 4D:
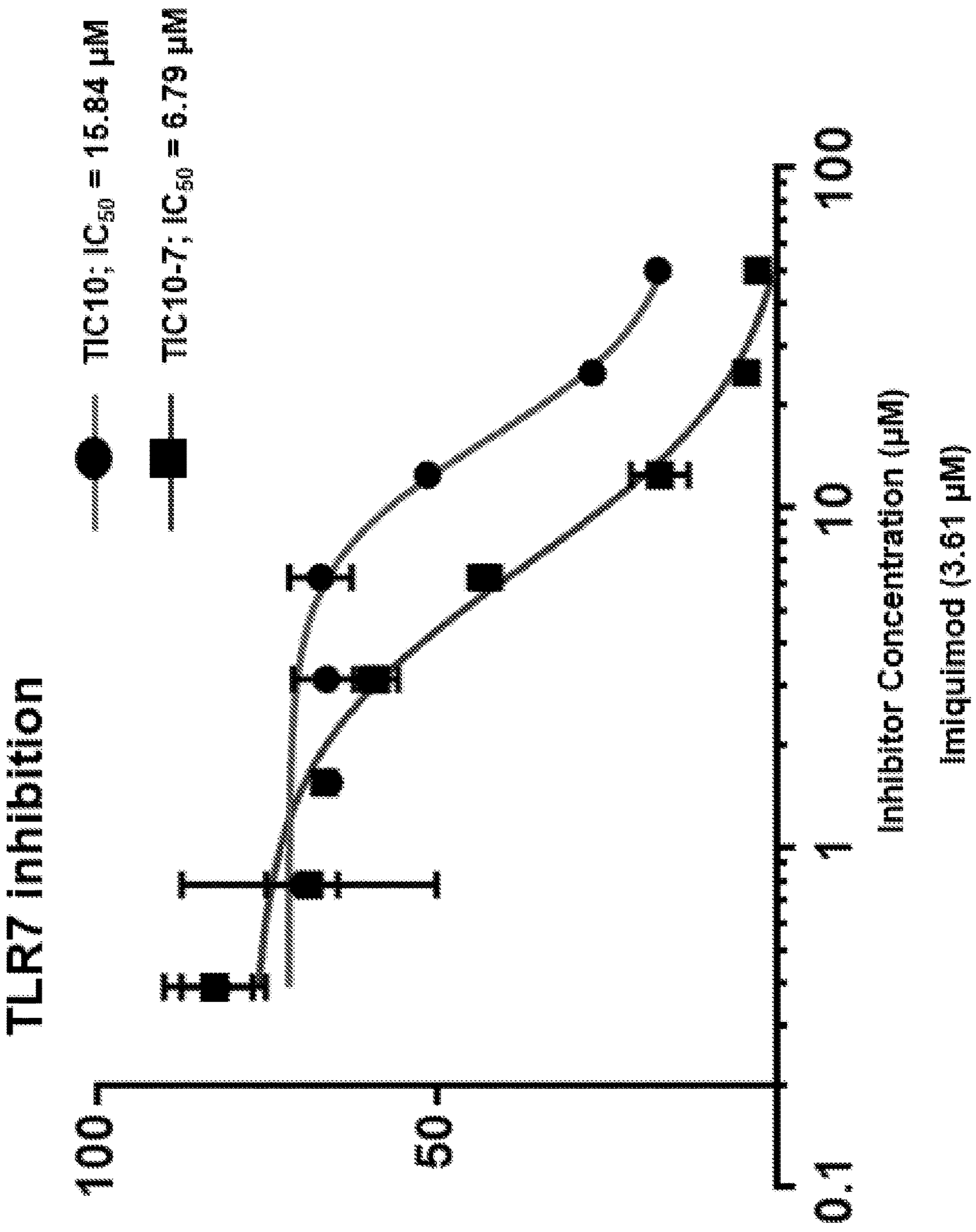
Figure 5A:
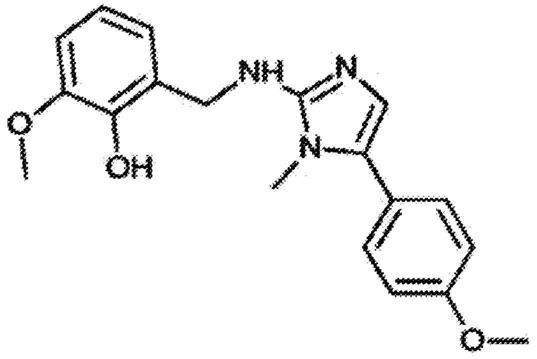
Figure 5A:
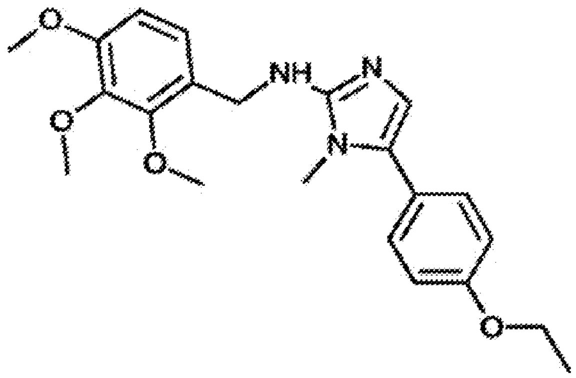
Figure 5A:
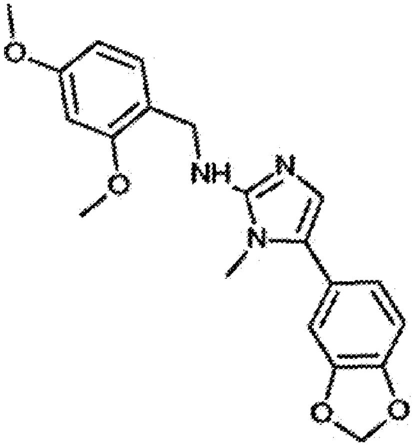
Figure 5A:
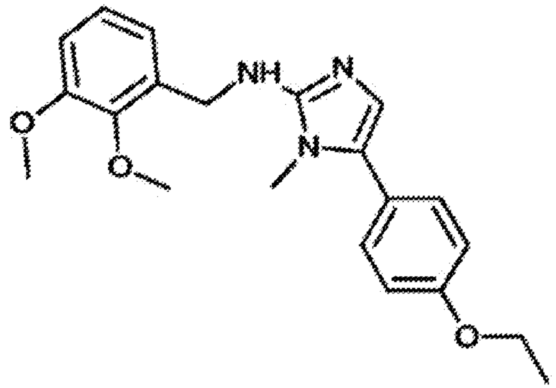
Figure 5A:
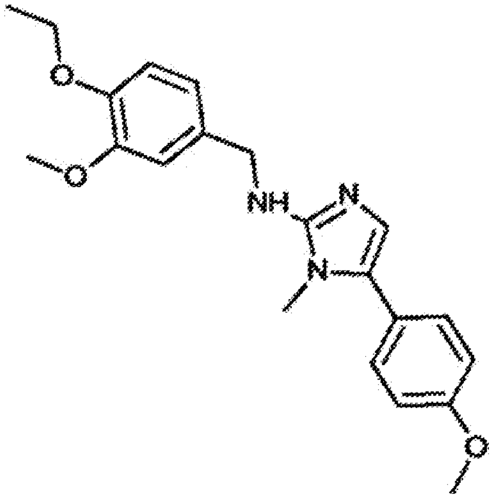
Figure 5A:
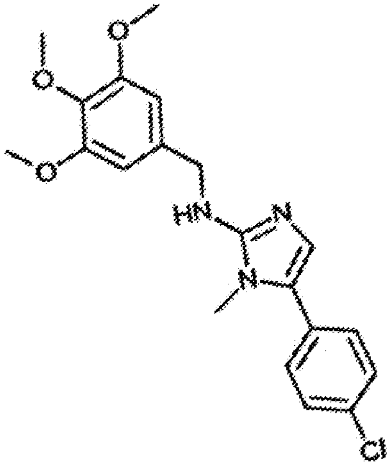

Based on the results of initial cell viability analysis, TIC10-1, TIC10-2, TIC10-5, TIC10-6, and TIC10-9 showed cytotoxicity and were excluded from subsequent experiments. The remaining derivatives, including TIC10, were subjected to RAW 264.7 cells followed by the stimulation with imiquimod or ODN2395. The three derivatives (TIC10-3, TIC10-7, and TIC10-8) exhibited improved inhibitory efficacy compared to TIC10 in a concentration dependent manner (FIGS. 4A and 4B). Among the active ligands (FIGS. 5A and 5B), TIC10-7 demonstrated a significant reduction in the TLR9-mediated TNF-α secretion level at both the concentrations tested (FIG. 4A) having an $IC_{50}$ value of 6.71 μM (FIG. 4C). Likewise, it inhibited the TLR7-mediated TNF-α secretion to a greater extent as compared to the other derivatives (FIG. 4B) having an $IC_{50}$ value of 6.79 μM (FIG. 4D), which matches its potency against TLR9. Consequently, this suggests that TIC10-7 ($C_{20}H_{21}N_3O_4$) can be an efficient dual inhibitor of TLR7/TLR9-related signaling pathways.

Figure 6A:
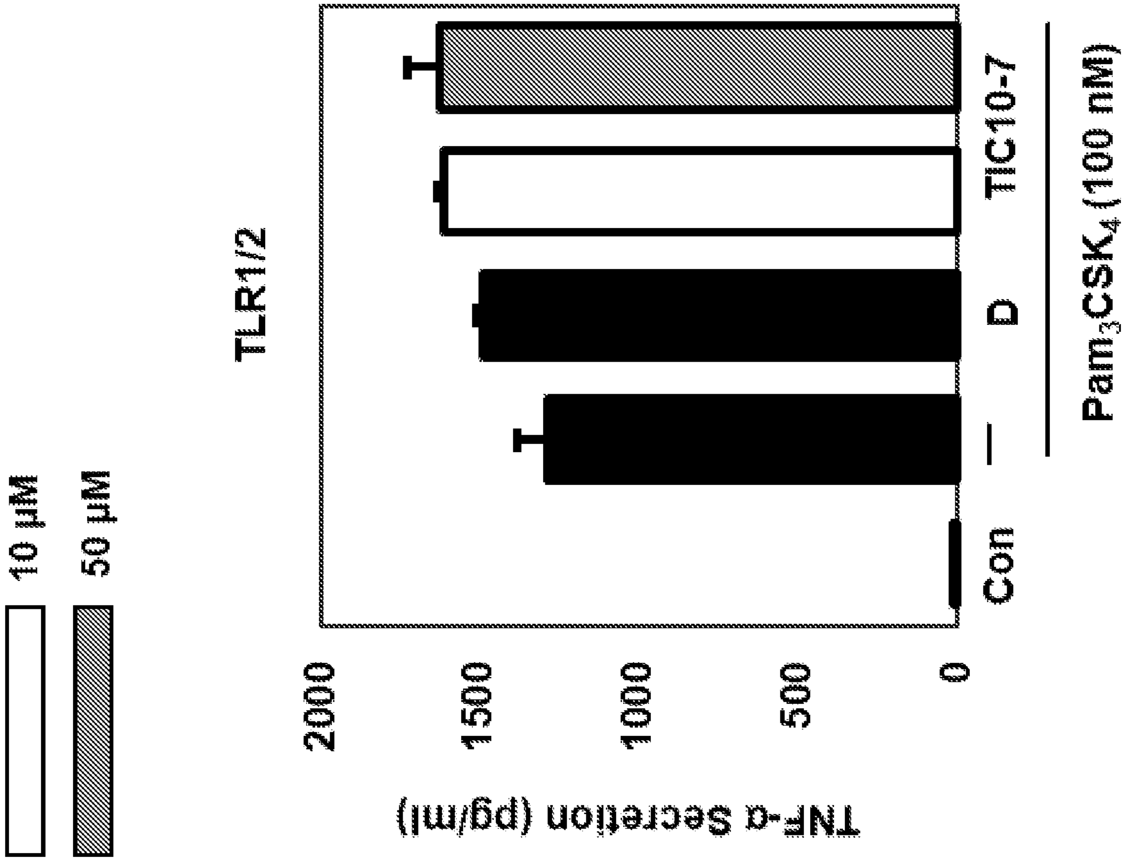
Figure 6B:
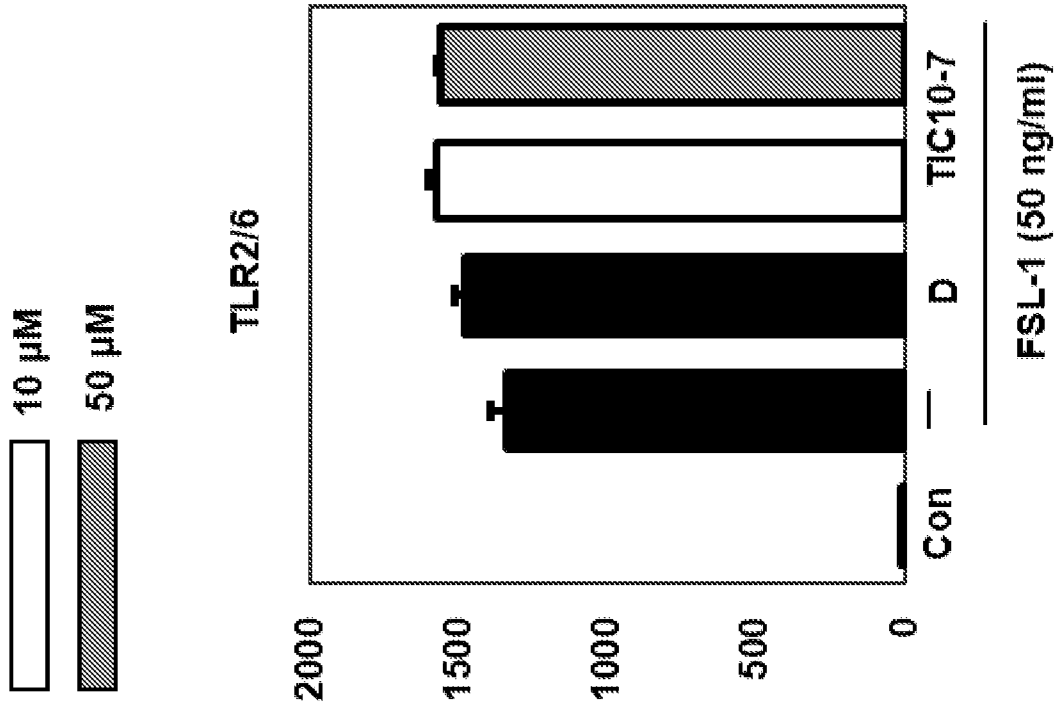
Figure 6C:
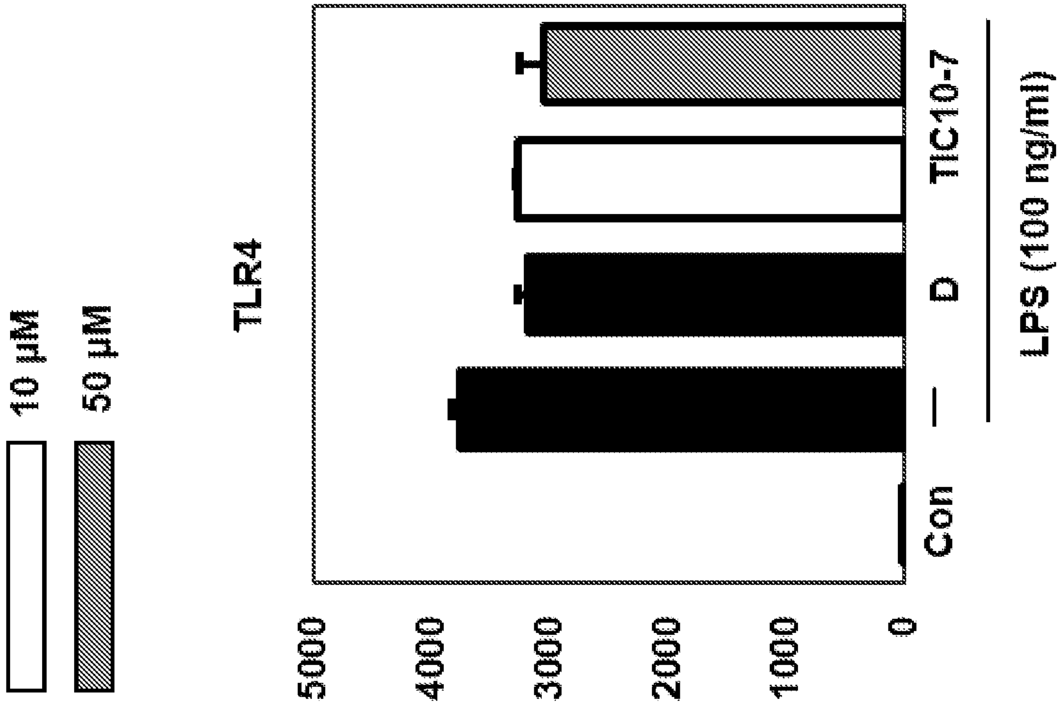
Figure 6D:
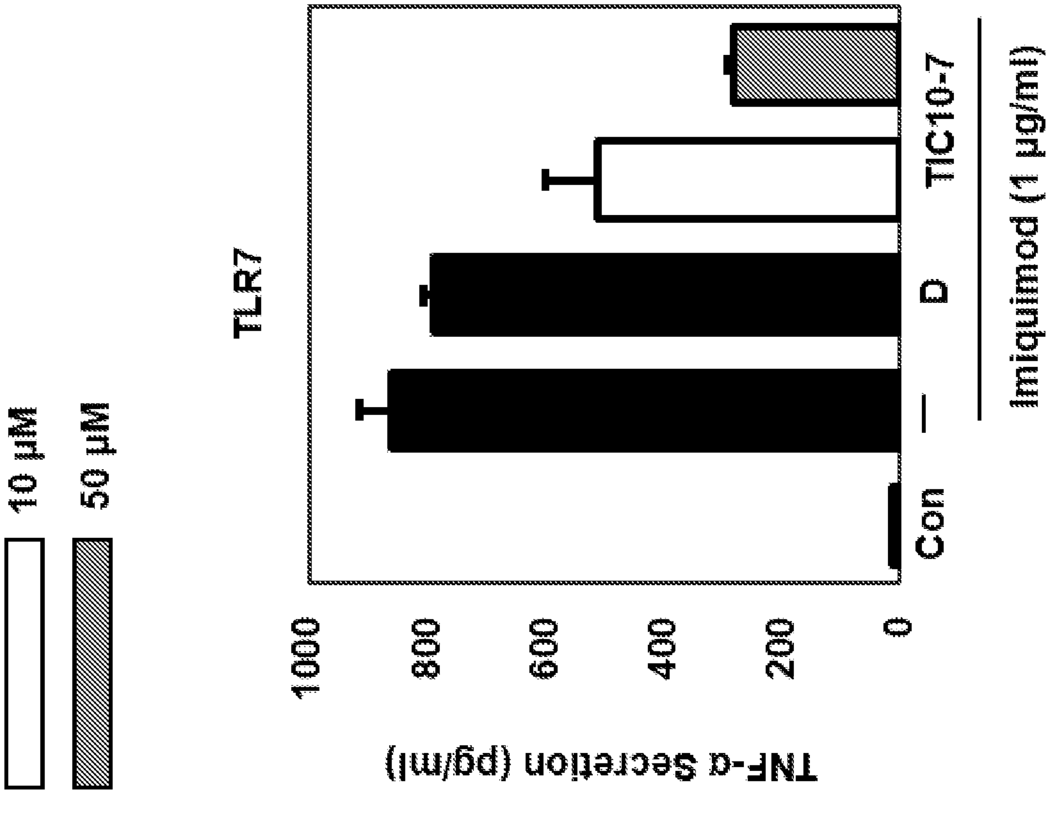
Figure 6E:
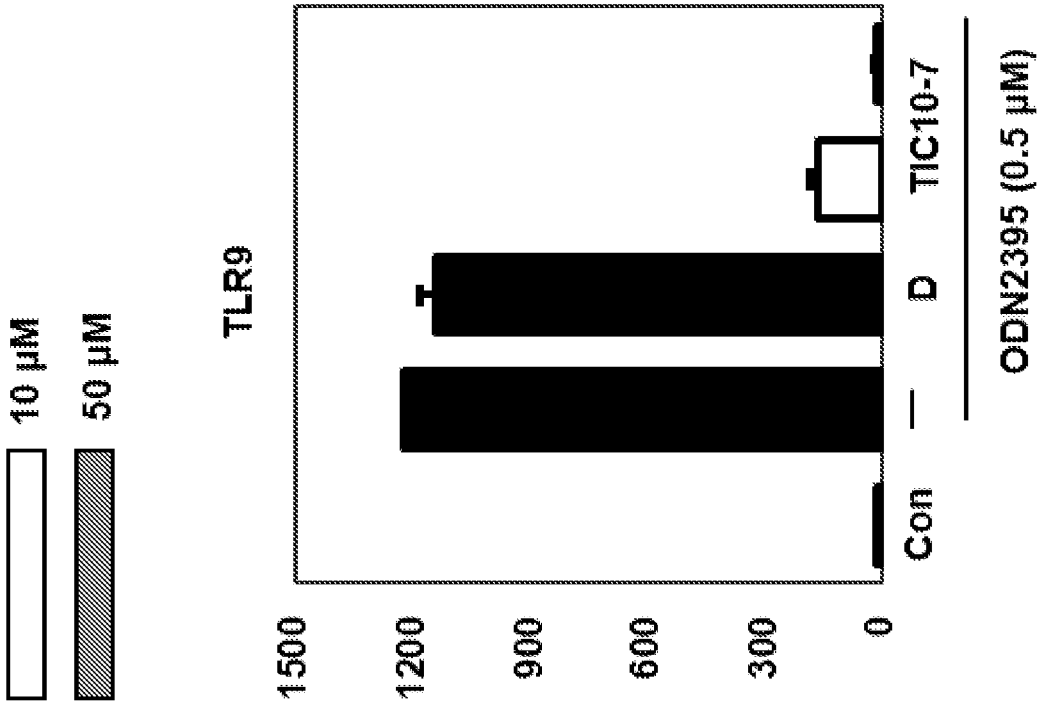
Figure 6F:
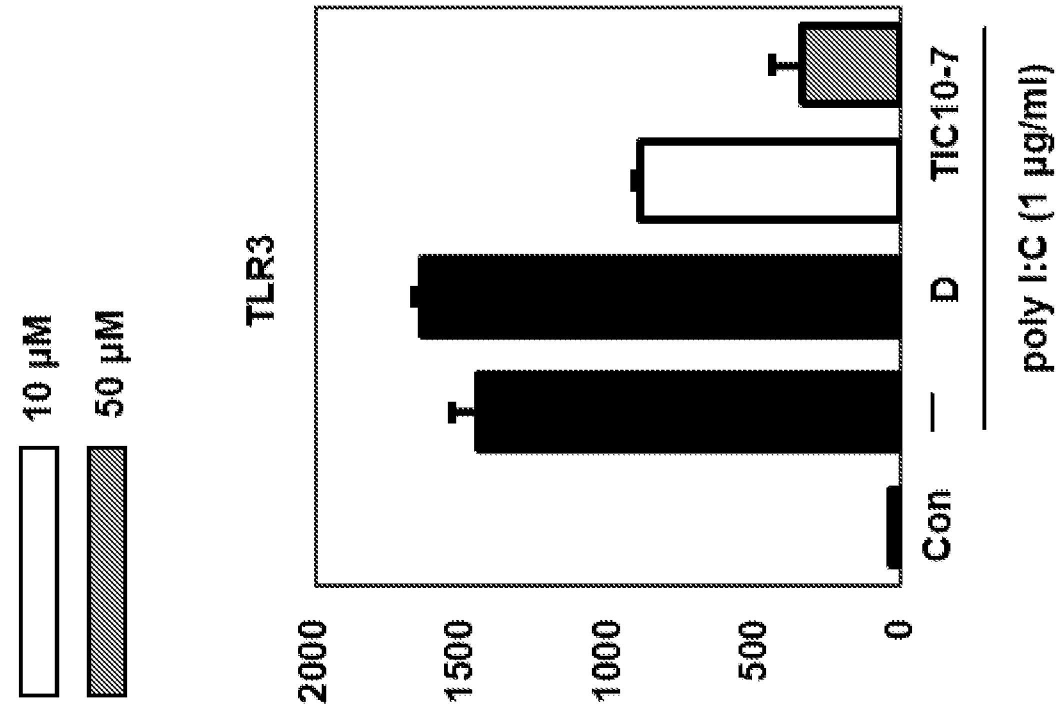
Figure 6G:
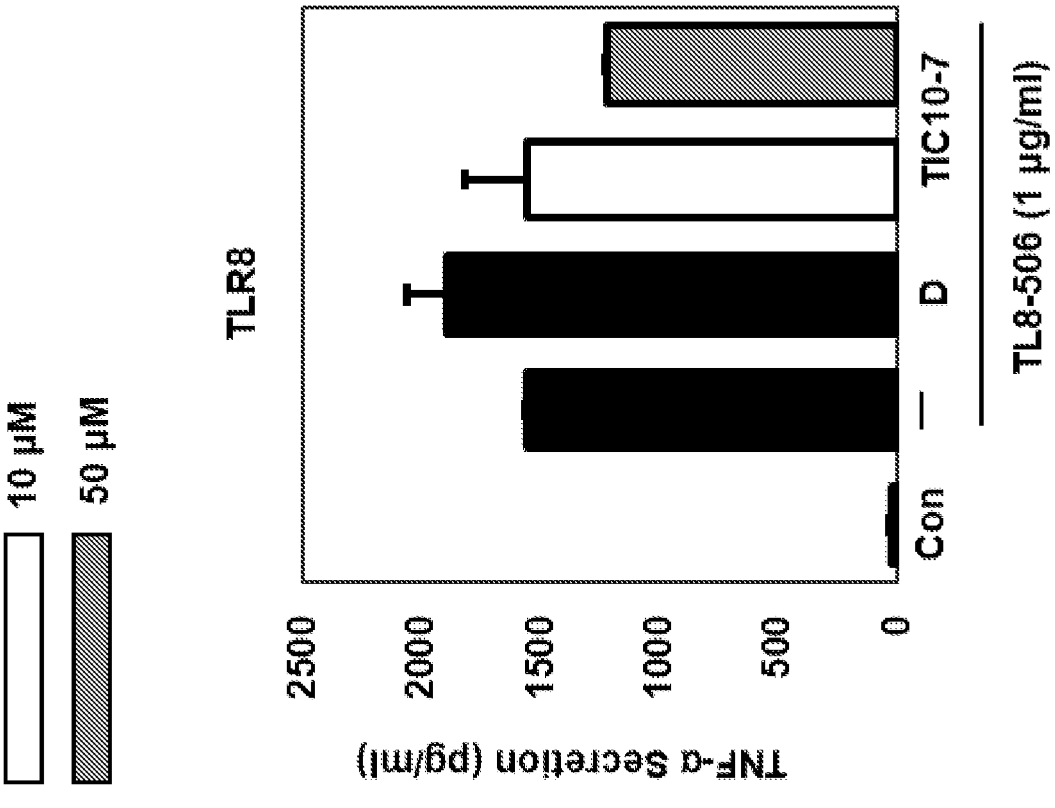

In order to determine the inhibitory effect of TIC10-7 on the cognate TLR-signaling pathway, RAW 264.7 cells were incubated with the ligand followed by the stimulation with different TLR agonists. The TLR agonists that were used were $Pam_3CSK_4$ (TLR1/2), FSL-1 (TLR2/6), lipopolysaccharide (LPS (TLR4)), poly I:C (TLR3), and TL8 (TLR8). Based on the results of measurement of TNF-α secretion level through ELISA, it was found that the inhibitor had no effect on surface TLR (TLR1/2, TLR2/6 and TLR4)-mediated cytokine production (FIGS. 6A to 6C). However, endosomal TLR (TLR3, TLR7 and TLR9)-mediated TNF-α secretion was observed to moderately reduced, while TLR8 being least affected (FIGS. 6D to 6G). This suggests that endosomal TLRs may exert a synergistic effect in which the negative regulation of one may affect the activity of the other under physiological conditions.

Figure 6H:
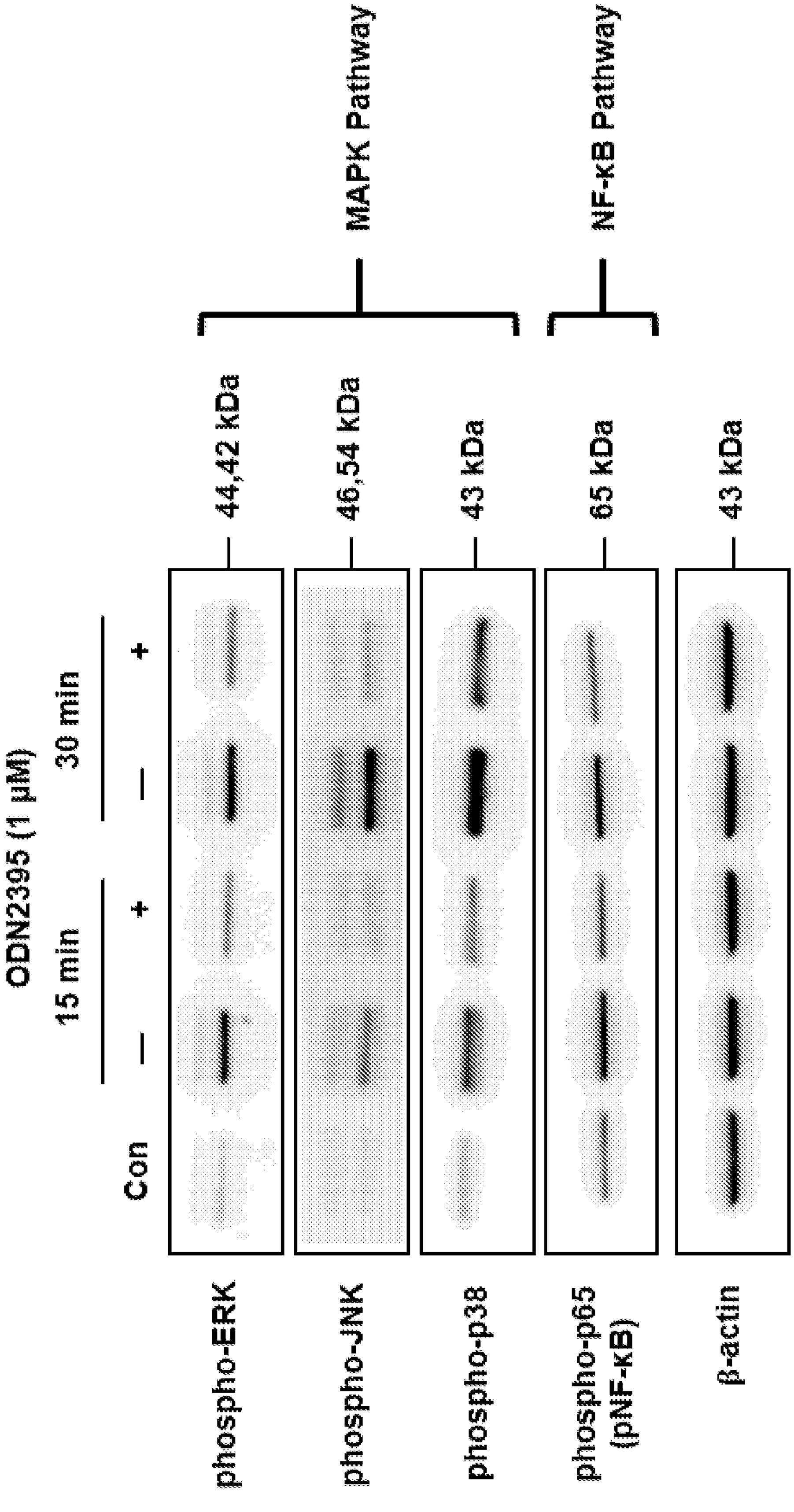

In general, MYD88 recruitment by TLRs triggers the activation of the transcription factor NF-κB as well as the cell proliferation factor MAPK. In order to identify the target signaling pathway of TIC10-7, a key downstream molecule was subjected to immunoblotting under co-treatment of ODN2395 and TIC10-7. Upon stimulation with ODN2395, TIC10-7 blocked the robust phosphorylation of MAPK (JNK, p38-MAPK, and ERK) and the p65 subunit of NF-κB at 15 min and 30 min (FIG. 6H). This suggests that the inhibitor is capable of interfering with the MYD88-dependent signaling pathway inducing the production of proinflammatory TNF-α.

Example 4: Confirmation of TIC10-7 Showing Analogous Binding Modes on TLR7 and TLR9

Figure 4E:
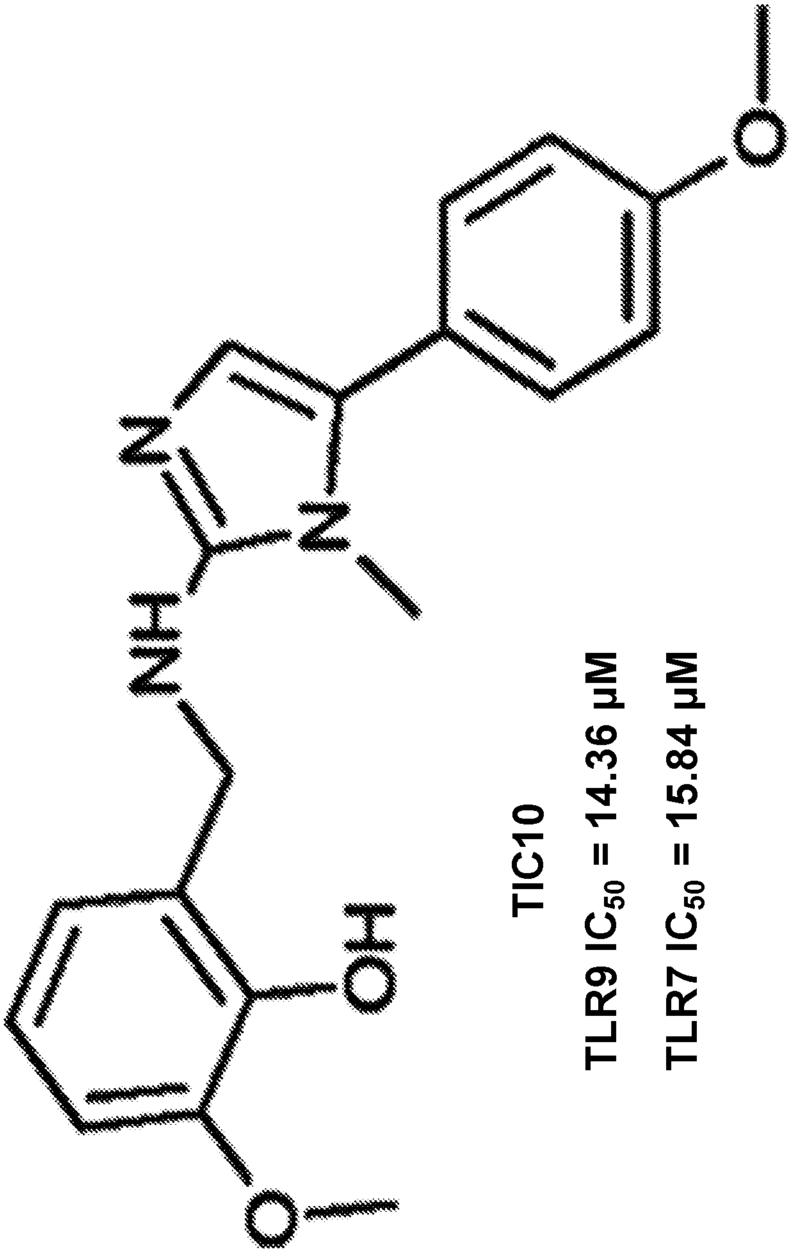
Figure 4F:
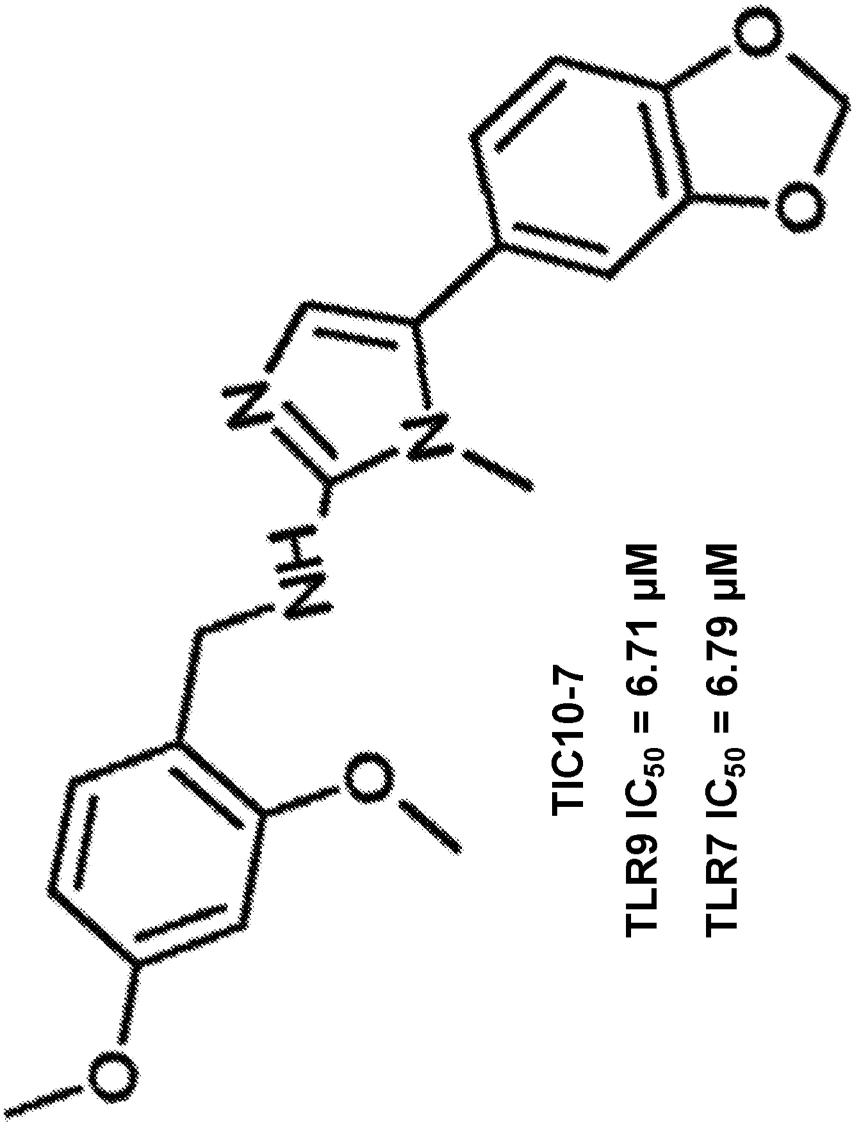

The initial hit TIC10 and the chemical derivative thereof contain a central imidazole (1H-imidazol-2-amine) moiety (FIG. 4E) representing one of the important scaffolds found in the endosomal TLR modulator (Yoo E. et al. (2013) *Org. Biomol. Chem.* 11(38):6526-6545). TIC10-7 comprises an 1,3-benzodioxole group, accompanied by a dimethoxyphenyl group attached to the central 1H-imidazol-2-amine (FIG. 4F), thereby providing a ligand having stronger inhibitory activity on TLR7 and TL9. Computational modeling showed that the docked ligand occupies the small molecule binding cavity of TLR7 and the same site on TLR9, exhibiting analogous binding modes. Based on the results of visual analysis of residues around about 5 Å from the ligand, it was confirmed that the intermolecular interaction was associated with amino acids similar to or distinct from those of the receptor binding cavity (FIGS. 7A and 7B).

Figure 7A:
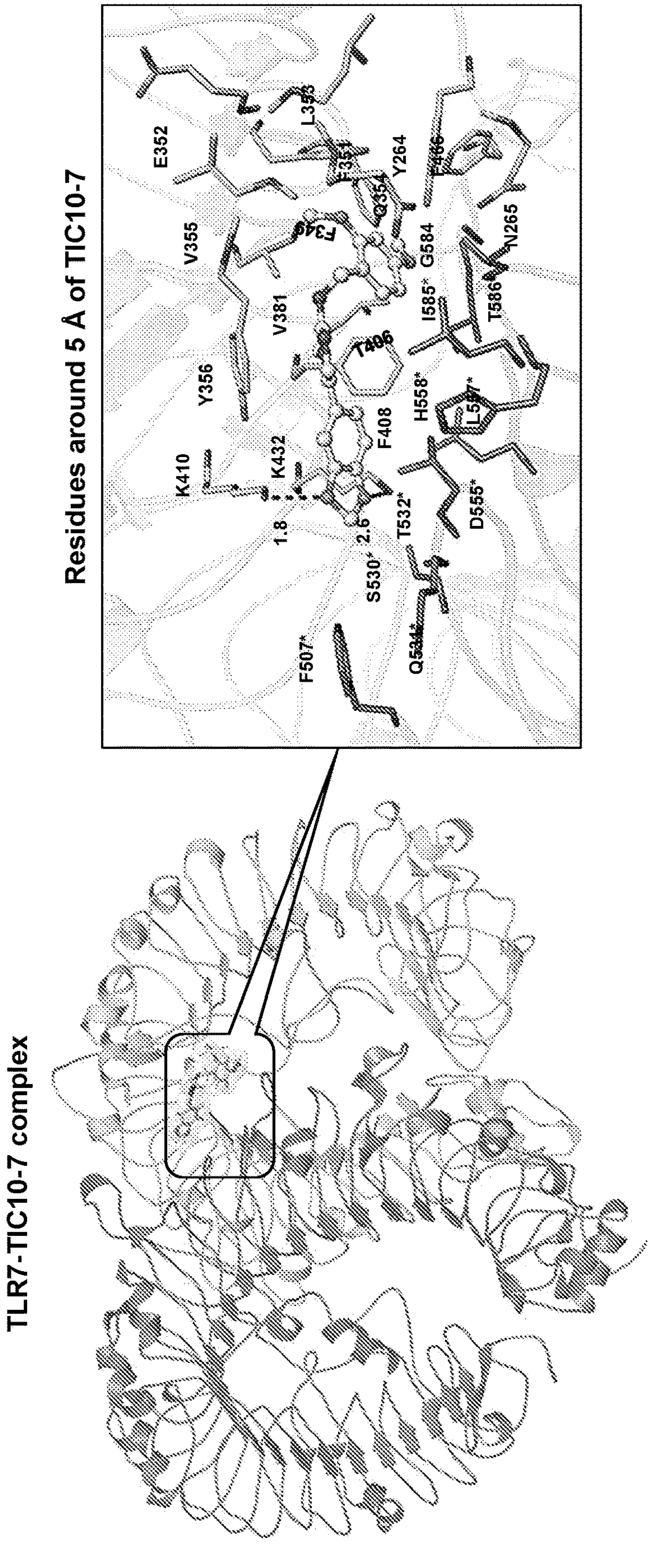
Figure 7B:
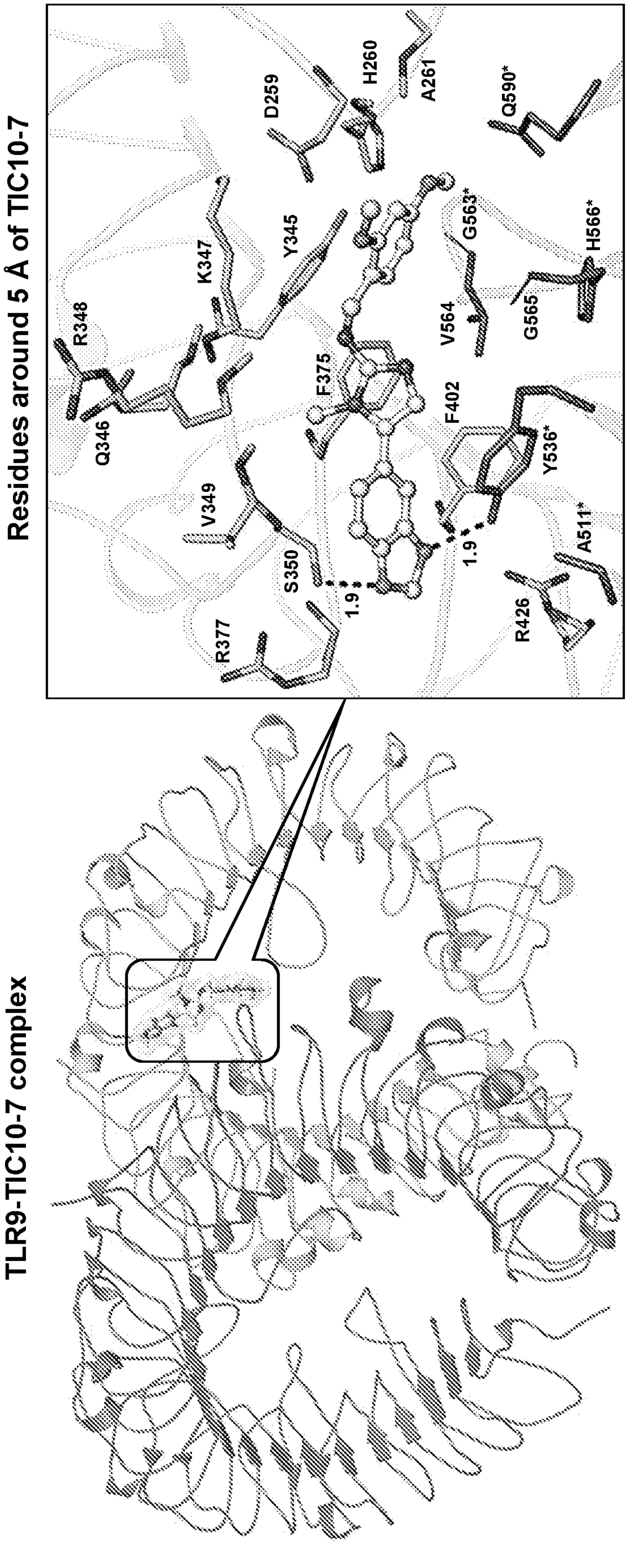

The interaction of TIC10-7 with TLR7 is similar to that of R848 (PDB ID: 5GMH) in that the central imidazole moiety is stabilized by a hydrophobic contact comprising residues F408, Y356, and L557* (FIG. 7A). The side chain of Y356 was aligned with the imidazole ring forming a partial π-stacking interaction. Oxygen atoms of the benzodioxole group formed hydrogen bonds with the side chain amino groups of K410 and K432. One oxygen atom of the dimethoxyphenyl group was involved in a close-range (~3.3 Å) electrostatic interaction with the side chain hydroxyl group of T586*, indicating the possibility of hydrogen bond. Moreover, the benzene ring of the dimethoxyphenyl group was connected to the hydrophobic pocket formed by residues F349, F351, V381, and F408. In addition, several other polar and non-polar residues were able to stabilize the ligand through van der Waals interactions.

In TLR9, the imidazole ring of TIC10-7 was stacked between the hydrophobic residues F375, F402 and Y536* (FIG. 7B) corresponding to V381, F408 and L557* of TLR7 (FIG. 7A). Two hydrogen bonds were formed between the oxygen atom of the benzodioxole group and the side chain hydroxyl groups of S350 and Y536*, which correspond to Y356 and L557* of TLR7. The dimethoxyphenyl group forms a hydrophobic contact with Y345 and electrostatic interactions with D259, H260 and Q590 of TLR9. In addition, residues D259, Y356, R348, R377, and G655* from site Ia (FIGS. 2A-2C) were found within a radius of 5 Å centered on the ligand, and they support in stabilization through electrostatic and van der Waals interactions.

INDUSTRIAL APPLICABILITY

According to the present invention, it is possible to obtain TIC10 ($C_{19}H_{21}N_3O_3$) and a derivative thereof TIC10-7 ($C_{20}H_{21}N_3O_4$), which are TLR inhibitory compounds that inhibit TLR7- and TLR9-mediated signaling pathways in vitro using the principle of computer-aided drug discovery. The novel compounds are capable of blocking the secretion of TNF-α by interfering with the expression and activation of NF-κB- and MAPK-related proinflammatory genes, and are thus useful as therapeutic agents for numerous autoimmune diseases, such as systemic lupus erythematosus (SLE), psoriasis, and psoriatic arthritis, which are associated with hyperactivity of nucleic-acid-sensing TLRs.

Although specific embodiments of the present invention have been disclosed in detail above, it will be obvious to those of ordinary skill in the art that the description is merely of preferable exemplary embodiments and is not to be construed as limiting the scope of the present invention. Therefore, the substantial scope of the present invention is to be defined by the appended claims and equivalents thereto.

The invention claimed is:

1. A compound of Chemical Formula 1 below or a pharmaceutically acceptable salt thereof:

[Chemical Formula 1]

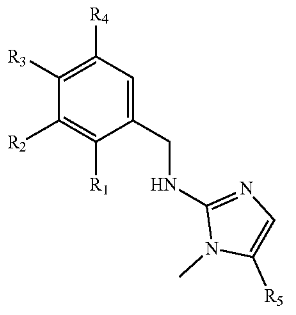

wherein in Chemical Formula 1, $R_1$ to $R_5$ are each independently a hydrogen atom, straight or branched alkyl, amino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, wherein the alkyl is $C_{1-30}$ alkyl, the alkoxy is $C_{1-30}$ alkoxy, the cycloalkyl is $C_{3-30}$ cycloalkyl, the allyl is $C_{2-30}$ allyl, the aryl is $C_{6-30}$ aryl, and the heteroaryl and heterocycloalkyl comprise a heteroatom selected from the group consisting of fluorine (F), oxygen (O), sulfur (S), and nitrogen (N), with the proviso that the compound, in which $R_1$ and $R_3$ are a hydrogen, $R_2$ or $R_4$ is methyl and $R_5$ is methoxyphenyl, is excluded.

2. The compound or the pharmaceutically acceptable salt thereof according to claim 1, wherein $R_5$ is represented by Chemical Formula 2 below:

[Chemical Formula 2]

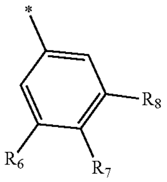

wherein in Chemical Formula 2, $R_6$ to $R_8$ are each independently a hydrogen atom, hydroxy, straight or branched alkyl, cycloalkyl, alkoxy, aryl, or halogen; or at least two of $R_6$ to $R_8$ are linked to each other to form a cycloalkyl or heterocycloalkyl, wherein the alkyl is $C_{1-30}$ alkyl, the alkoxy is $C_{1-30}$ alkoxy, the cycloalkyl is $C_{3-30}$ cycloalkyl, the aryl is $C_{6-30}$ aryl, and the heterocycloalkyl comprises a heteroatom selected from the group consisting of fluorine (F), oxygen (O), sulfur(S), and nitrogen (N).

3. The compound or the pharmaceutically acceptable salt thereof according to claim 2, wherein $R_5$ is represented by Chemical Formula 3 below:

[Chemical Formula 3]

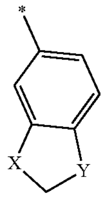

wherein in Chemical Formula 3,

X or Y is each independently oxygen (O), sulfur(S), or nitrogen (N).

4. The compound or the pharmaceutically acceptable salt thereof according to claim 1, wherein $R_1$ is a hydrogen atom, hydroxy, or methoxy; $R_2$ is a hydrogen atom or methoxy; $R_3$ is a hydrogen atom, methoxy, or ethoxy; $R_4$ is a hydrogen atom or methoxy; and $R_5$ is chlorophenyl, ethoxyphenyl, or 1,3-benzodioxolyl.

5. The compound or the pharmaceutically acceptable salt thereof according to claim 1, wherein the compound is any one compound selected from the group consisting of Chemical Formula 1-1, I-2, I-3, I-4, I-5, and I-6:

[Chemical Formula 1-1]

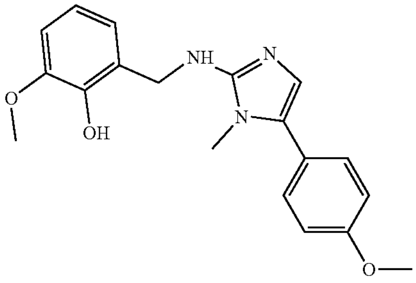

;

-continued

[Chemical Formula 1-2]

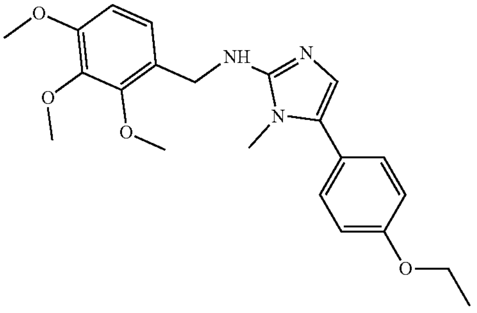

;

[Chemical Formula 1-3]

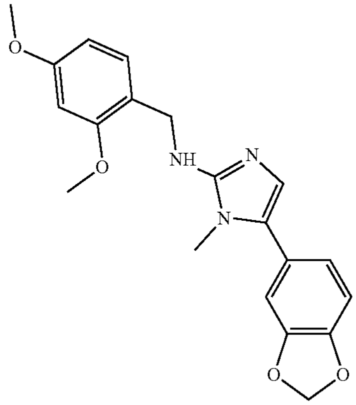

;

[Chemical Formula 1-4]

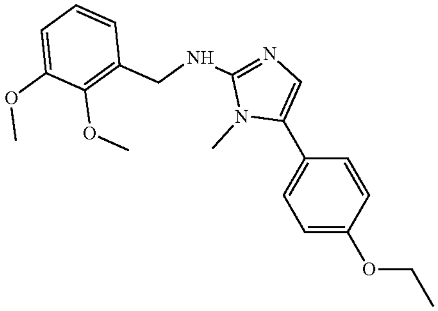

;

[Chemical Formula 1-5]

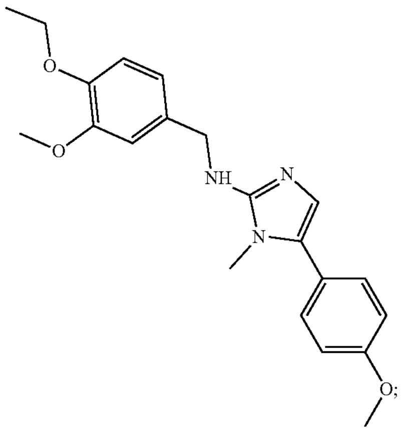

; and

-continued

[Chemical Formula 1-6]

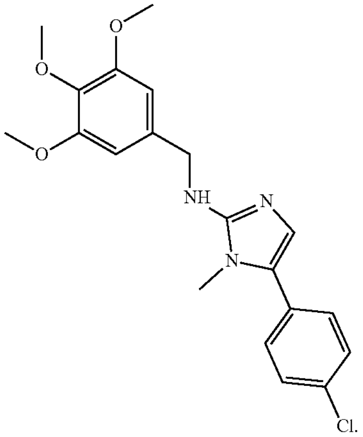

6. A composition comprising a compound of Chemical Formula 1 below or a pharmaceutically acceptable salt thereof:

[Chemical Formula 1]

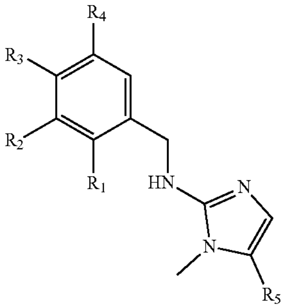

wherein in Chemical Formula 1, $R_1$ to $R_5$ are each independently a hydrogen atom, straight or branched alkyl, amino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, wherein the alkyl is $C_{1-30}$ alkyl, the alkoxy is $C_{1-30}$ alkoxy, the cycloalkyl is $C_{3-30}$ cycloalkyl, the allyl is $C_{2-30}$ allyl, the aryl is $C_{6-30}$ aryl, and the heteroaryl and heterocycloalkyl comprise a heteroatom selected from the group consisting of fluorine (F), oxygen (O), sulfur (S), and nitrogen (N), with the proviso that the compound, in which $R_1$ and $R_3$ are a hydrogen, $R_2$ or $R_4$ is methyl and $R_5$ is methoxyphenyl, is excluded.

7. The composition according to claim 6, wherein $R_5$ is represented by Chemical Formula 2 below:

[Chemical Formula 2]

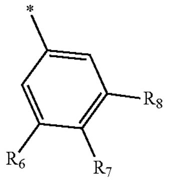

wherein in Chemical Formula 2, $R_6$ to $R_8$ are each independently a hydrogen atom, hydroxy, straight or branched alkyl, cycloalkyl, alkoxy, aryl, or halogen; or at least two of $R_6$ to $R_8$ are linked to each other to form a cycloalkyl or heterocycloalkyl, wherein the alkyl is $C_{1-30}$ alkyl, the alkoxy is $C_{1-30}$ alkoxy, the cycloalkyl is $C_{3-30}$ cycloalkyl, the aryl is $C_{6-30}$ aryl, and the heterocycloalkyl comprises a heteroatom selected from the group consisting of fluorine (F), oxygen (O), sulfur(S), and nitrogen (N).

8. The composition according to claim 7, wherein $R_5$ is represented by Chemical Formula 3 below:

[Chemical Formula 3]

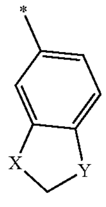

wherein in Chemical Formula 3,

X or Y is each independently oxygen (O), sulfur(S), or nitrogen (N).

9. The composition according to claim 6, wherein $R_1$ is a hydrogen atom, hydroxy, or methoxy; $R_2$ is a hydrogen atom or methoxy; $R_3$ is a hydrogen atom, methoxy, or ethoxy; $R_4$ is a hydrogen atom or methoxy; and $R_5$ is chlorophenyl, ethoxyphenyl, or 1,3-benzodioxolyl.

10. The composition according to claim 6, wherein the compound of Chemical Formula 1 is any one compound selected from the group consisting of Chemical Formula 1-1, I-2, I-3, I-4, I-5, and I-6 below:

[Chemical Formula 1-1]

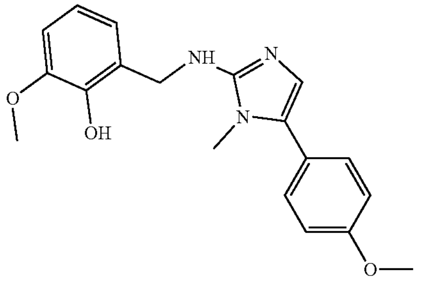

;

-continued

[Chemical Formula 1-2]

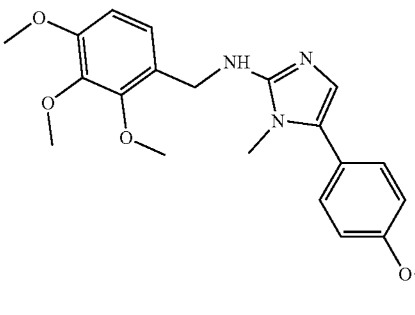

;

[Chemical Formula 1-3]

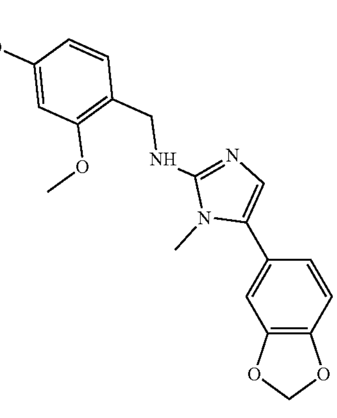

;

[Chemical Formula 1-4]

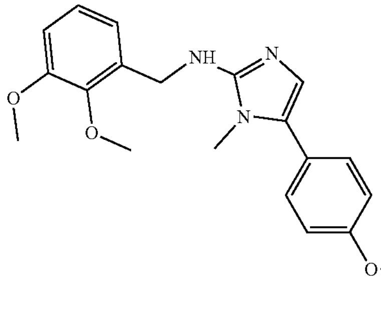

;

[Chemical Formula 1-5]

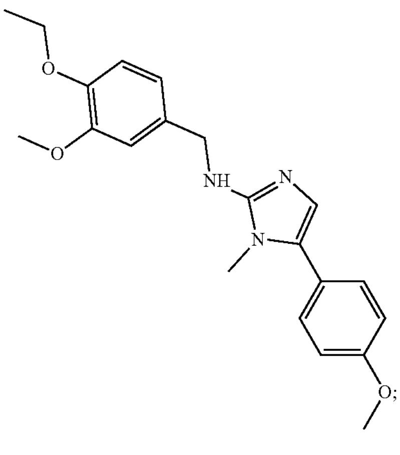

; and

-continued

[Chemical Formula 1-6]

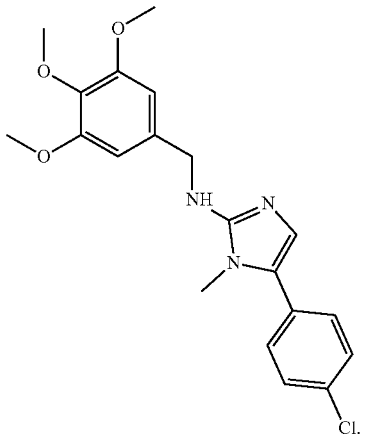

11. The composition according to claim 6, wherein the compound of Chemical Formula 1 inhibits a signaling pathway of at least one TLR (toll-like receptor) selected from the group consisting of TLR7, TLR9, TLR3, and TLR8.

12. The composition according to claim 6, wherein the compound of Chemical Formula 1 performs at least one selected from the group consisting of:

inhibition of secretion of TNF-α (tumor necrosis factor-α);

inhibition of activation of NF-κB (nuclear factor k-light-chain-enhancer of activated B cells); and inhibition of activation of MAPKs (mitogen-activated protein kinases).

13. A method for treating an autoimmune disease in a subject in need thereof, comprising administering to the subject a composition comprising a compound of Chemical Formula 1 below or a pharmaceutically acceptable salt thereof:

[Chemical Formula 1]

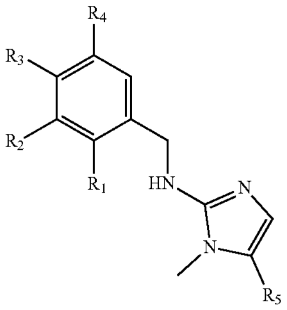

wherein in Chemical Formula 1, $R_1$ to $R_5$ are each independently a hydrogen atom, straight or branched alkyl, amino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, wherein the alkyl is $C_{1-30}$ alkyl, the alkoxy is $C_{1-30}$ alkoxy, the cycloalkyl is $C_{3-30}$ cycloalkyl, the allyl is $C_{2-30}$ allyl, the aryl is $C_{6-30}$ aryl, and the heteroaryl and heterocycloalkyl comprise a heteroatom selected from the group consisting of fluorine (F), oxygen (O), sulfur (S), and nitrogen (N), wherein the autoimmune disease is associated with toll-like receptor (TLR) signaling pathway.

14. The method according to claim 13, wherein the autoimmune disease is selected from the group consisting of systemic lupus erythematosus, psoriasis, psoriatic arthritis, rheumatoid arthritis, experimental autoimmune arthritis, asthma, Crohn's disease, multiple sclerosis, experimental autoimmune encephalomyelitis, myasthenia gravis, thyroiditis, experimental forms of uveitis, Hashimoto's thyroiditis, primary myxedema, thyrotoxicosis, pernicious anemia, autoimmune atrophic gastritis, Addison's disease, premature menopause, male infertility, childhood diabetes, Goodpasture's syndrome, pemphigus vulgaris, pemphigoid, sympathetic ophthalmitis, lens-induced uveitis, autoimmune hemolytic anemia, idiopathic leukopenia, primary sclerosing cholangitis, chronic active hepatitis, latent cirrhosis, ulcerative colitis, Sjogren's syndrome, scleroderma, Wegener's granulomatosis, polymyositis, dermatomyositis, and discoid lupus.

15. A method for treating an inflammatory disease in a subject in need thereof, comprising administering to the subject a composition comprising a compound of Chemical Formula 1 below or a pharmaceutically acceptable salt thereof:

[Chemical Formula 1]

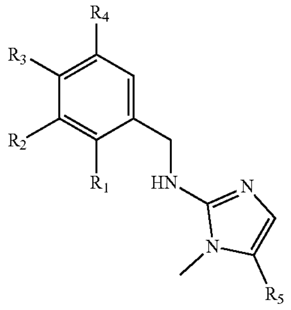

wherein in Chemical Formula 1, $R_1$ to $R_5$ are each independently a hydrogen atom, straight or branched alkyl, amino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, wherein the alkyl is $C_{1-30}$ alkyl, the alkoxy is $C_{1-30}$ alkoxy, the cycloalkyl is $C_{3-30}$ cycloalkyl, the allyl is $C_{2-30}$ allyl, the aryl is $C_{6-30}$ aryl, and the heteroaryl and heterocycloalkyl comprise a heteroatom selected from the group consisting of fluorine (F), oxygen (O), sulfur (S), and nitrogen (N), wherein the inflammatory disease is associated with the toll-like receptor (TLR) signaling pathway.

16. The method according to claim 15, wherein the inflammatory disease is selected from the group consisting of insulin-dependent diabetes mellitus, eczema, allergies, atopic dermatitis, acne, atopic rhinitis, pulmonary inflammation, allergic dermatitis, chronic sinusitis, contact dermatitis, seborrheic dermatitis, gastritis, gout, gouty arthritis, ulcers, chronic bronchitis, ulcerative colitis, ankylosing spondylitis, sepsis, angiitis, bursitis, temporal arteritis, solid cancers, Alzheimer's disease, arteriosclerosis, obesity, viral infection, and nonalcoholic steatohepatitis.

17. A method for inhibiting a toll-like receptor (TLR) in a subject in need thereof, comprising administering an effective amount of a compound of Chemical Formula 1 below or a pharmaceutically acceptable salt thereof to the subject:

[Chemical Formula 1]

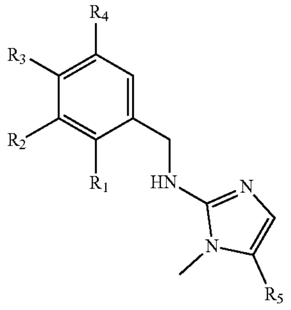

wherein in Chemical Formula 1, $R_1$ to $R_5$ are each independently a hydrogen atom, straight or branched alkyl, amino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, wherein the alkyl is $C_{1-30}$ alkyl, the alkoxy is $C_{1-30}$ alkoxy, the cycloalkyl is $C_{3-30}$ cycloalkyl, the allyl is $C_{2-30}$ allyl, the aryl is $C_{6-30}$ aryl, and the heteroaryl and heterocycloalkyl comprise a heteroatom selected from the group consisting of fluorine (F), oxygen (O), sulfur (S), and nitrogen (N).

18. The method according to claim 17, wherein the TLR is TLR7, TLR9, TLR3, TLR8, or a combination thereof.

19. The method according to claim 18, wherein the administering of the effective amount of the compound or pharmaceutically acceptable salt thereof results in:

inhibition of secretion of TNF-α (tumor necrosis factor-α);

inhibition of activation of NF-κB (nuclear factor k-light-chain-enhancer of activated B cells); and/or inhibition of activation of MAPKs (mitogen-activated protein kinases).

20. A method for treating a toll-like receptor (TLR) signaling pathway-associated disease or disorder in a subject in need thereof, comprising administering an effective amount of a compound of Chemical Formula 1 below or a pharmaceutically acceptable salt thereof to the subject:

[Chemical Formula 1]

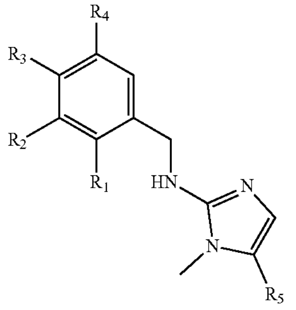

wherein in Chemical Formula 1, $R_1$ to $R_5$ are each independently a hydrogen atom, straight or branched alkyl, amino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, wherein the alkyl is $C_{1-30}$ alkyl, the alkoxy is $C_{1-30}$ alkoxy, the cycloalkyl is $C_{3-30}$ cycloalkyl, the allyl is $C_{2-30}$ allyl, the aryl is $C_{6-30}$ aryl, and the heteroaryl and heterocycloalkyl comprise a heteroatom selected from the group consisting of fluorine (F), oxygen (O), sulfur (S), and nitrogen (N), wherein the TLR signaling pathway-associated disease or disorder is inflammation or autoimmune disease.

* * * * *